US011840576B2

(12) United States Patent
Jordan et al.

(10) Patent No.: US 11,840,576 B2
(45) Date of Patent: *Dec. 12, 2023

(54) METHODS FOR TREATING NEPHROTIC SYNDROME

(71) Applicant: CEDARS-SINAI MEDICAL CENTER, Los Angeles, CA (US)

(72) Inventors: Stanley Jordan, Manhattan Beach, CA (US); Ashley Vo, Northridge, CA (US); Jua Choi, Porter Ranch, CA (US)

(73) Assignee: Cedars-Sinai Medical Center, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/498,278

(22) Filed: Oct. 11, 2021

(65) Prior Publication Data
US 2022/0098317 A1    Mar. 31, 2022

Related U.S. Application Data

(63) Continuation of application No. 15/779,711, filed as application No. PCT/US2016/066033 on Dec. 9, 2016, now Pat. No. 11,149,091.

(60) Provisional application No. 62/265,322, filed on Dec. 9, 2015.

(51) Int. Cl.
C07K 16/28    (2006.01)
A61P 13/12    (2006.01)
A61K 39/00    (2006.01)

(52) U.S. Cl.
CPC .......... *C07K 16/2887* (2013.01); *A61P 13/12* (2018.01); *A61K 2039/505* (2013.01); *A61K 2039/54* (2013.01); *A61K 2039/545* (2013.01); *C07K 2317/24* (2013.01); *C07K 2317/732* (2013.01)

(58) Field of Classification Search
None
See application file for complete search history.

(56) References Cited

U.S. PATENT DOCUMENTS

| | | | |
|---|---|---|---|
| 11,149,091 B2 | 10/2021 | Jordan et al. | |
| 2009/0311255 A1* | 12/2009 | Brunetta | A61P 13/12 424/130.1 |
| 2014/0314748 A1* | 10/2014 | Gokarn | C07K 16/2887 424/153.1 |
| 2016/0346387 A1 | 12/2016 | Brunetta | |
| 2020/0207864 A1 | 7/2020 | Jordan et al. | |

FOREIGN PATENT DOCUMENTS

| | | | |
|---|---|---|---|
| WO | 2017004091 A1 | 1/2017 | |
| WO | 2017100722 A1 | 6/2017 | |

OTHER PUBLICATIONS

Nozu et al., Pediatr. Nephrol. vol. 20, pp. 1660-1663, 2005. (Year: 2005).*
Gulati et al. Clin. J. Am. Soc. Nephro. vol. 5, pp. 2207-2212, 2010. (Year: 2010).*
Smith, Grahm Pediatr Nephrol. vol. 22, pp. 893-898, 2007. (Year: 2007).*
Brown et al., ('Obinutuzumab plus fludarabine/cyclophosphamide or bendamustine in the initial therapy of CLL patients: the phase 1b GALTON trial'.)Blood vol. 125, No. 16, pp. 2779-2785, 2015, (Year: 2015).*
Sehn et al. (A phase 1 study of obinutuzumab induction followed by 2 years of maintenance in patients with relapsed CD20-positive B-cell malignancies)Blood. vol. 119, No. 22, pp. 5118-5125, 2012.*
Basu et al. (Ofatumumab for Rituximab-Resistant Nephrotic Syndrome)N.Engl. J. Med. vol. 370 No. 13, pp. 1268-1270, 2014.*
Segarra et al. Clinical Journal of AMerican Society of Nephrology 4(16) p. 1083-1088 Jun. 2009.*
Sethi et al., Obinutuzumab is Effective for the Treatment of Refractory Membranous Nephropathy, Kidney International Reports, 2020, vol. 5, pp. 1510-1531.
Choi et al., First Experience with Obinutuzumab (Type II Anti-CD20) in Patients with Treatment-Resistant Glomerular Diseases and Antibody-Mediated Rejection, Am J Transplant, 2016, vol. 16(3), Abstract Only.
Clinical Trial NCT02550652 retrieved from: [https://clinicaltrials.gov/ct2/history/NCT02550652?A=1&B=1&C=merged] on Aug. 5, 2020, 12 pages.
Mossner et al., Increasing the Efficacy of CD20 Antibody Therapy through the Engineering of a New Type II Anti-CD20 Antibody with Enhanced Direct and Immune Effector Cell-Mediated B-cell Cytotoxicity, Blood, 2010, vol. 115(22), pp. 4393-4402.
"Genentech's Gazyva (obinutuzumab), in Combination With Standard of Care, More Than Doubles the Percentage of Lupus Nephritis Patients Achieving Complete Renal Response, Compared to Standard of Care Alone" retrieved from: [https://www.gene.com/media/press-releases/14821/2019-11-09/genentechs-gazyva-obinutuzumab-in-combin], 2019.
"FDA grants Breakthrough Therapy Designation for Roche's Gazyva (obinutuzumab) in Lupus Nephritis" retrieved from: [https://www.roche.com/media/releases/med-cor-2019-09-18.htm], 2019.
International Search Report and Written Opinion of PCT Application No. PCT/US2016/066033, dated Mar. 3, 2017, 9 Pages.
Basu et al., Ofatumumab for Rituximab-Resistant Nephrotic Syndrome, 2014, N. Engl. J. Med, vol. 370(13), pp. 1268-1270.
Brown et al., Obinutuzumab Plus Fludarabine/Cyclophosphamide or Bendamustine in the Initial Therapy of CLL Patients: The Phase 1b GALTON Trial, 2015, Blood, vol. 125(18), pp. 2779-2785.
Goede et al., Obinutuzumab Plus Chlorambucil in Patients with CLL and Coexisting Conditions, 2014, N. Engl. J. Med., vol. 370(12), pp. 1101-1110.

(Continued)

*Primary Examiner* — Jana A Hines
*Assistant Examiner* — Khatol S Shahnan Shah
(74) *Attorney, Agent, or Firm* — Nixon Peabody LLP; Linda B. Huber; Suwei Zhu

(57) ABSTRACT

Described herein are methods for treating nephrotic syndrome using an anti-CD20 antibody. In one embodiment, that anti-CD20 antibody is Obinutuzumab.

20 Claims, 10 Drawing Sheets

(56) References Cited

OTHER PUBLICATIONS

Sehn et al., A Phase 1 Study of Obinutuzumab Induction Followed by 2 Years of Maintenance in Patients with Relapsed CD20-Positive B-cell Malignancies, 2012, Blood, vol. 119(22), pp. 5118-5125.
Gulati et al., Efficacy and Safety of Treatment with Rituximab for Difficult Steroid-Resistant and Dependant Nephrotic Syndrome: Multicentric Report, Clin. J. Am. Soc. Nephro., 2010, vol. 5, pp. 2207-2212.
Smith et al., Is there a Role for Rituximab in the Treatment of Idiopathic Childhood Nephrotic Syndrome?, Pediatr Nephrol, 2007, vol. 22, pp. 893-898.
Vo et al., Benefits of Rituximab Combined with Intravenous Immunoglobulin for Desensitization in Kidney Transplant Recipients, Transplantation, 2014, vol. 98(3), pp. 312-319.
Clinical trials.gov, Phase II Study to Evaluate the Efficacy of IdeS to Desensitize Transplant Patients with Positive Crossmatch Test (HighIdeS), Mar. 30, 2017, Clinical Trials. Gov Identifier: NCT02790437, 3 Pages.
Jordan et al., IgG Endopeptidase in Highly Sensetized Patients Undergoing Transplantation, The New England Journal of Medicine, 2017, vol. 377(5), pp. 442-453.
Jordan et al., Experience with the Bacterial Enzyme IdeS (IgG Endopeptidase) for Desensitization of Highly-HLA Sensitized (HS) Kidney Allograft Recepients, Abstract 166, 2017 American Transplant Congress, Retrieved from: [https://atcmeetingabstracts.com/abstract/experience-with-the-bacterial-enzyme-ides-igg-endopeptidase-for-desensitization-of-highly-hla-sensitized-hs-kidney-allograft-recipients/].
Jordan et al., Follow Up Patients Treated with the IgG Endopeptidase (IdeS) for Desensitization and HLA Incompatible (HLAi) Kidney Transplantation, Abstract 523, 2018 American Transplant Congress, Retrieved from: [https://atcmeetingabstracts.com/abstract/follow-up-of-patients-treated-with-the-igg-endopeptidase-ides-for-desensitization-and-hla-incompatible-hlai-kidney-transplantation/].
Loupy et al., Combined Posttransplant Prophylactic IVIg/Anti-CD 2-/Plasmapheresis in Kidney Recipients with Preformed Donor-Specific Antibodies: A Pilot Study, Transplantation, 2010, vol. 89(11), pp. 1403-1410.
Marfo et al., Desensitization Protocols and Their Outcome, Clin J Am Soc Nephrol, 2011, vol. 6, pp. 922-936.
Shehata et al., The Use of Immunoglobulin Therapy for Patients Undergoing Solid Organ Transplantation: An Evidence-Based Practice Guideline, Transfusion Medicine Reviews, 2010, vol. 24(1), pp. S7-S27.
Hychko et al., A Systematic Review and Meta-Analysis of Rituximab in Antibody-Mediated Renal Allograft Rejection, Int. J. Organ Transplant Med., 2011, vol. 2(2), pp. 51-56.
Vo et al. Rituximab and Intravenous Immune Globulin for Desensitization during Renal Transplantation. The New England Journal of Medicine (2008). 359:242-51.
Vo et al. Efficacy, Outcomes, and Cost-Effectiveness of Desensitization Using IVIG and Rituximab. Transplantation (2013). 95:852-858.
Asante-Korang et al., Outcomes in highly sensitized pediatric heart transplant patients using current management strategies, The Journal of Heart and Lung Transplantation, 2015, vol. 34, pp. 175-181.
Jordan et al., Imlifidase Desensitization in Crossmatch-positive, Highly Sensitized Kidney Transplant Recipients: Results of an International Phase 2 Trial (Highdes), Transplatation, 2021, vol. 105(8), pp. 1808-1817.
Fehr et al., Rituximab and Intravenous Immunoglobulin Treatment of Chronic Antibody-Mediated Kidney Allograft Rejection, Clinical and Translational Research, Transplantation, 2009, vol. 87(12), pp. 1837-1841.
Zachary et al., Rituximab Prevents an Anamnestic Response in Patients With Cryptic Sensitization to HLA, Clinical and Translational Research, Transplantation, 2013, vol. 95(5), pp. 701-704.
Kahwaji et al., Six-year outcomes in broadly HLA-sensitized living donor translplant recipients desensitized with intravenous immunoglobulin and rituximab, Transplant International, 2016, vol. 29, pp. 1276-1285.
Billing et al., Successful Treatment of Chronic Antibody-Mediated Rejection With IVIG and Rituximab in Pediatric Renal Transplant Recipients, Transplantation, 2008, vol. 86(9), pp. 1214-1221.
Clinical trials.gov, Phase II Study, Evaluation of Safety and Efficacy of IdeS in Chronic Kidney Disease, V. 1, Aug. 22, 2014, Clinical Trials.Gov Identifier: NCT02224820, 7 Pages.
Clinical trials.gov, Phase II Study, Evaluation of Safety and Efficacy of IdeS in Chronic Kidney Disease, V. 2, Mar. 17, 2015, Clinical Trials.Gov Identifier: NCT02224820, 6 Pages.
Clinical trials.gov, Phase II Study, Evaluation of Safety and Efficacy of IdeS in Chronic Kidney Disease, V. 3, Apr. 19, 2016, Clinical Trials.Gov Identifier: NCT02224820, 15 Pages.
Clinical trials.gov, Phase II Study, Evaluation of Safety and Efficacy of IdeS in Chronic Kidney Disease, V. 4, Jan. 18, 2017, Clinical Trials.Gov Identifier: NCT02224820, 2018, 15 Pages.
Clinical trials.gov, Ides in Highly Sensitized Patients Awaiting Kidney Transplantation, V. 1, Apr. 24, 2015, Clinical Trials.Gov Identifier: NCT02426684, 8 Pages.
Clinical trials.gov, Ides in Highly Sensitized Patients Awaiting Kidney Transplantation, V. 2, Jun. 17, 2015, Clinical Trials.Gov Identifier: NCT02426684, 8 Pages.
Clinical trials.gov, Ides in Highly Sensitized Patients Awaiting Kidney Transplantation, V. 3, Oct. 7, 2016, Clinical Trials.Gov Identifier: NCT02426684, 9 Pages.
Clinical trials.gov, Ides in Highly Sensitized Patients Awaiting Kidney Transplantation, V. 4, Sep. 25, 2017, Clinical Trials.Gov Identifier: NCT02426684, 8 Pages.
Clinical trials.gov, Study to Evaluate the Safety, Tolerability, Efficacy and PK of IdeS in Kidney Transplantation, V. 1, Jun. 17, 2015, Clinical Trials.Gov Identifier: NCT02475551, 7 Pages.
Clinical trials.gov, Study to Evaluate the Safety, Tolerability, Efficacy and PK of IdeS in Kidney Transplantation, V. 2, Jun. 22, 2015, Clinical Trials.Gov Identifier: NCT02475551, 7 Pages.
Clinical trials.gov, Study to Evaluate the Safety, Tolerability, Efficacy and PK of IdeS in Kidney Transplantation, V. 3, May 23, 2016, Clinical Trials.Gov Identifier: NCT02475551, 7 Pages.
Clinical trials.gov, Study to Evaluate the Safety, Tolerability, Efficacy and PK of IdeS in Kidney Transplantation, V. 4, Sep. 7, 2016, Clinical Trials.Gov Identifier: NCT02475551, 7 Pages.
Clinical trials.gov, Study to Evaluate the Safety, Tolerability, Efficacy and PK of IdeS in Kidney Transplantation, V. 5, Jan. 11, 2017, Clinical Trials.Gov Identifier: NCT02475551, 7 Pages.
Clinical trials.gov, Study to Evaluate the Safety, Tolerability, Efficacy and PK of IdeS in Kidney Transplantation, V. 6, Jan. 18, 2017, Clinical Trials.Gov Identifier: NCT02475551, 7 Pages.
Clinical trials.gov, Study to Evaluate the Safety, Tolerability, Efficacy and PK of IdeS in Kidney Transplantation, V. 7, Jul. 11, 2017, Clinical Trials.Gov Identifier: NCT02475551, 7 Pages.
Clinical trials.gov, Study to Evaluate the Safety, Tolerability, Efficacy and PK of IdeS in Kidney Transplantation, V. 8, Jan. 5, 2018, Clinical Trials.Gov Identifier: NCT02475551, 7 Pages.

* cited by examiner

Segmental WBCs

Granular IgG

Subepi, mesangial deposits; small TRS

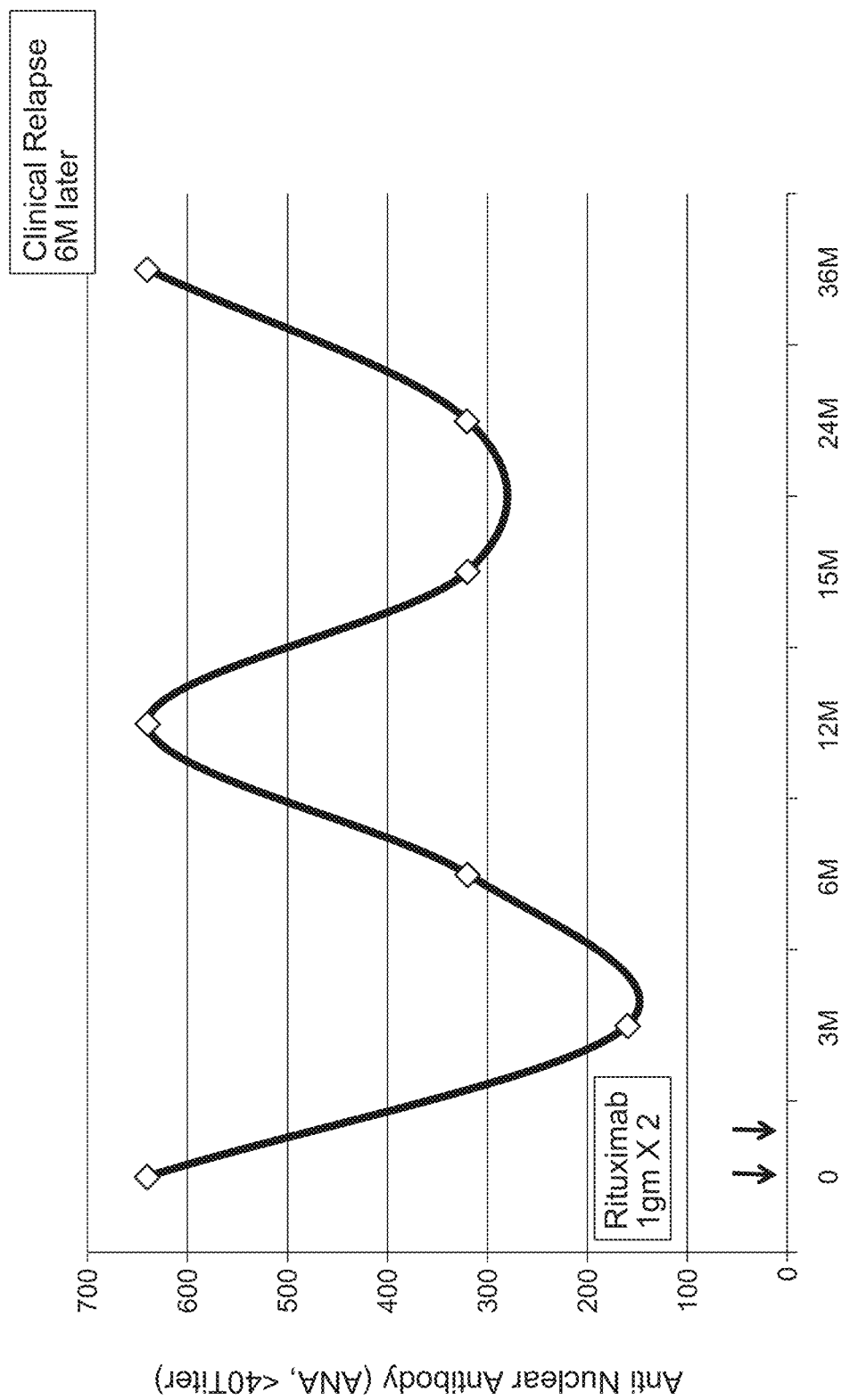

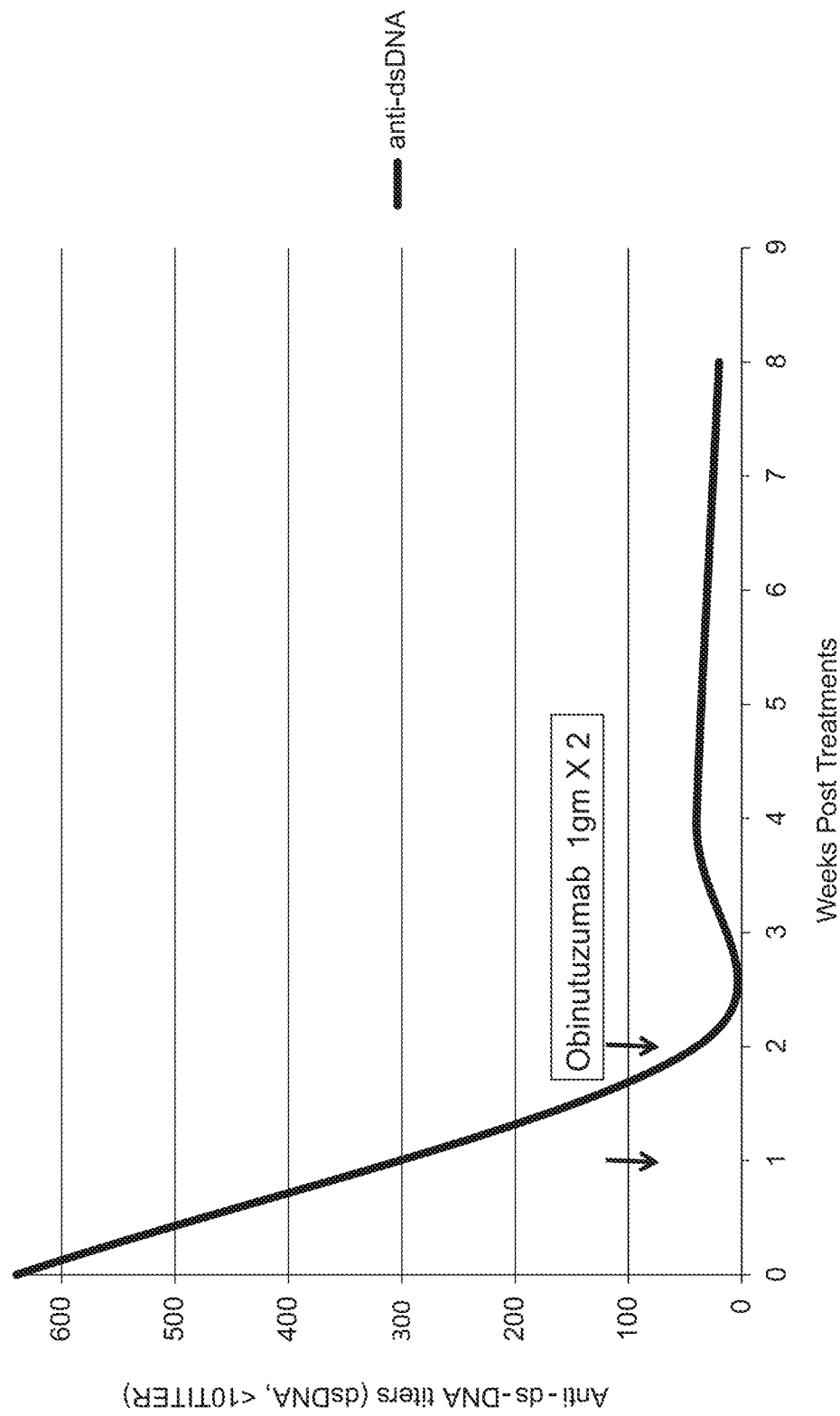

METHODS FOR TREATING NEPHROTIC SYNDROME

CROSS-REFERENCE TO RELATED APPLICATION

This application is a continuation of U.S. patent application Ser. No. 15/779,711 filed May 29, 2018, which is a National Phase of International Application No. PCT/US2016/066033 filed Dec. 9, 2016, which designated the U.S. and that International Application was published under PCT Article 21(2) in English, which also claims the benefit of U.S. Provisional Application No. 62/265,322, filed Dec. 9, 2015. The entire contents of each of the aforementioned applications in incorporated herein by reference.

TECHNICAL FIELD

The invention relates to treatment for nephrotic syndrome, including Rituximab-resistant nephrotic syndrome.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Nephrotic syndrome (NS) is a group of symptoms that include protein in the urine, low blood protein levels, high cholesterol levels, high triglyceride levels and swelling. NS is caused by different disorders that damage the kidneys and results in release of too much protein in the urine. Exemplary conditions that result in NS include cancer, genetic disorders, immune disorders, diabetes, systemic lupus, multiple myeloma, infections and so on.

Obinutuzumab (Obi) is a novel FDA approved glycol-rich monoclonal antibody which binds CD20 at a different epitope than Rituximab, another anti-CD20 antibody also approved by the FDA. Thus, Obinutuzumab has been termed a type 2 anti-CD20 and also has a different mechanism of action than Rituximab. Obi depletes B-cells primarily through homotropic aggregation and antibody-dependent cellular cytotoxicity. These features give it many distinctions from Rituximab. The differences in mechanism of action between Obi and Rituximab are shown in FIG. 1. Obi was thought to be more effective in depleting B-cells in remote areas of the body such as the spleen and lymph nodes which could still act as mediators of disease. Indeed, this was found to be true in the pivotal trials of Obi in chronic lymphocytic leukemia and non-Hodgkin's Lymphoma (NHL) where Obi was found superior to Rituximab in inducing long-term remissions of these diseases. Analysis of lymphoid and splenic tissues from treated patients showed a marked difference in removal of CD20+ tumor cells in Obi patients compared to Rituximab.

Due to either significant side effects or relative inefficacies of many existing therapeutic agents for nephrotic syndrome, there is an unmet clinical need for novel therapies for treatment of nephrotic syndrome that are more effective and less toxic. Most patients with NS have an immunologic cause for the disease and current therapies are directed to modification of the immune system. There are no FDA approved therapies and current therapies have to be maintained on a daily basis, often for life which is often toxic with limited efficacy. Accordingly, provided herein are methods for treating nephrotic syndrome using Obinutuzumab.

SUMMARY

The following embodiments and aspects thereof are described and illustrated in conjunction with compositions and methods which are meant to be exemplary and illustrative, not limiting in scope.

Provided herein are methods for treating, inhibiting or reducing severity of nephrotic syndrome in a subject in need thereof comprising, consisting of or consisting essentially of providing an anti-CD20 antibody and administering an effective amount of the antibody to the subject, so as to treat, inhibit or reduce the severity of nephrotic syndrome in the subject.

Also provided herein are methods for treating, inhibiting or reducing severity of nephrotic syndrome in a subject in need thereof comprising, consisting of or consisting essentially of administering an effective amount of an anti-CD20 antibody to the subject, so as to treat, inhibit or reduce the severity of nephrotic syndrome in the subject.

Further provided herein are methods are treating, inhibiting or reducing severity of glomerulonephritis (GN) in a subject in need thereof comprising, consisting of or consisting essentially of providing an anti-CD20 antibody; and administering an effective amount of the antibody to the subject, so as to treat, inhibit or reduce the severity of glomerulonephritis in the subject.

Also provided herein are methods are treating, inhibiting or reducing severity of glomerulonephritis (GN) in a subject in need thereof comprising, consisting of or consisting essentially of administering an effective amount of an anti-CD20 antibody to the subject, so as to treat, inhibit or reduce the severity of glomerulonephritis in the subject.

In some embodiments, glomerulonephritis is membranous glomerulonephritis, focal segmental glomerulosclerosis (FSGS), minimal change nephrotic syndrome, cryoglobulinemic glomerulonephritis, IgA nephropathy.

In some embodiments, the anti-CD20 antibody is Obinutuzumab, Rituximab or a combination there. In one embodiment, the anti-CD20 antibody is Obinutuzumab.

In one embodiment, the subject has drug-resistant nephrotic syndrome. In an embodiment, the drug-resistant nephrotic syndrome is Rituximab-resistant nephrotic syndrome.

In some embodiments, nephrotic syndrome in the subject is caused by any one or more of minimal change disease (MCD), focal segmental glomerulosclerosis (FSGS), membranous glomerulonephritis (MGN), IgA nephropathy and cryoglobulinemic glomerulonephritis.

In some embodiments, the subject has been administered standard-of-care treatment prior to administration of anti-CD20 antibody. In an embodiment, the subject does not respond to standard-of-care treatment prior to administration of anti-CD20 antibody.

In some embodiments, the subject has not been administered standard-of-care treatment prior to administration of anti-CD20 antibody. In some embodiments, the anti-CD20 antibody is administered simultaneously or sequentially with standard-of-care treatment.

In some embodiments, the standard-of-care treatments are any one or more of high dose prednisone (steroids), mycophenolic acid (CELLCEPT®) and optionally calcineurin inhibitors. In some embodiments, the calcineurin inhibitors are cyclosporine, tacrolimus, or a combination thereof.

In some embodiments, the effective amount of the anti-CD20 antibody (for example, is Obinutuzumab) is about 0.01-0.05 mg/kg/day, 0.05-0.1 mg/kg/day, 0.1 to 0.5 mg/kg/day, 0.5 to 1 mg/kg/day, 1 to 2 mg/kg/day, 2 to 3 mg/kg/day, 3 to 4 mg/kg/day, 0.5 to 5 mg/kg/day, 1 to 5 mg/kg/day, 3 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the anti-CD20 antibody (for example, is Obinutuzumab) is administered to the subject before, during, or after the subject develops nephrotic syndrome. In some embodiments, the anti-CD20 antibody (for example, is Obinutuzumab) is administered to the subject 1-3 times per day or 1-7 times per week. In some embodiments, the anti-CD20 antibody (for example, is Obinutuzumab) is administered to the subject for 1-5 days, 1-5 weeks, 1-5 months, or 1-5 years.

In various embodiments, the anti-CD20 antibody or fragment thereof is administered to the subject before, during, or after the subject develops the nephrotic syndrome. In some embodiments, the anti-CD20 antibody or a fragment thereof is administered to the subject 1-3 times per day or 1-7 times per week. In some embodiments, the anti-CD20 antibody or a fragment thereof is administered to the subject for 1-5 days, 1-5 weeks, 1-5 months, or 1-5 years.

In some embodiments, the subject has been administered standard-of-care treatment for nephrotic syndrome prior to administration of the anti-CD20 antibody (for example, prior to administration of Obinutuzumab). In some embodiments, the subject does not respond to or poorly responds to standard-of-care treatment for nephrotic syndrome prior to administration of anti-CD20 antibody (for example, Obinutuzumab). In some embodiments, the subject has not been administered standard-of-care treatment for nephrotic syndrome prior to administration of anti-CD20 antibody (for example, Obinutuzumab). In some embodiments, the standard-of-care treatment for nephrotic syndrome is administered simultaneously or sequentially with the anti-CD20 antibody (for example, Obinutuzumab).

In exemplary embodiments, the standard-of-care treatment for nephrotic syndrome is steroid, cyclophosphamide, cyclosporine, tacrolimus and Rituximab. Nephrotic syndrome treatments include high dose prednisone (steroids), mycophenolic acid (CELLCEPT®) and occasionally calcineurin inhibitors (cyclosporine and tacrolimus). All are used in various combinations. In addition, high dose Cytoxan is used in severe cases. This has a high side effect profile and is not used routinely. Because of this, and the relative inefficacy of many of the drugs, there is a large unmet need for new therapies that are less toxic in patients with nephrotic syndrome Also provided herein are methods for treating, inhibiting or reducing severity of nephrotic syndrome in a subject in need thereof comprising, consisting of or consisting essentially of providing an anti-CD20 antibody and administering an effective amount of an anti-CD20 antibody to the subject, so as to treat, inhibit or reduce the severity of nephrotic syndrome in the subject. In one embodiment, the effective amount of the antibody is two doses of 1 gram Obinutuzumab per dose. In some embodiments, Obinutuzumab is administered intravenously. In some embodiment, the two doses of 1 gram per dose of Obinutuzumab are administered about 15 days apart. In some embodiments, a first dose is administered on the same day or split over a period of two days. In an embodiment, the first dose is split over two days wherein 100 mg of Obinutuzumab is administered on day 1 and 900 mg of Obinutuzumab is administered on day 2. In some embodiments, effective amount of the Obinutuzumab is administered to the subject every 6 months, every 1 year, every 18 months, every 2 years, every 3 years, every 4 years, every 5 years, every 10 year, for lifetime of the subject or combinations thereof. In an embodiment, the subject is human.

Also provided herein are methods for treating, inhibiting or reducing severity of nephrotic syndrome in a subject in need thereof comprising, consisting of or consisting essentially of administering an effective amount of an anti-CD20 antibody to the subject, so as to treat, inhibit or reduce the severity of nephrotic syndrome in the subject. In one embodiment, the effective amount of the antibody is two doses of 1 gram Obinutuzumab per dose. In some embodiments, Obinutuzumab is administered intravenously. In some embodiment, the two doses of 1 gram per dose of Obinutuzumab are administered about 15 days apart. In some embodiments, a first dose is administered on the same day or split over a period of two days. In an embodiment, the first dose is split over two days wherein 100 mg of Obinutuzumab is administered on day 1 and 900 mg of Obinutuzumab is administered on day 2. In some embodiments, effective amount of the Obinutuzumab is administered to the subject every 6 months, every 1 year, every 18 months, every 2 years, every 3 years, every 4 years, every 5 years, every 10 year, for lifetime of the subject or combinations thereof. In an embodiment, the subject is human.

Further provided herein are methods are treating, inhibiting or reducing severity of glomerulonephritis (GN) in a subject in need thereof comprising, consisting of or consisting essentially of providing an anti-CD20 antibody and administering an effective amount of the antibody to the subject, so as to treat, inhibit or reduce the severity of glomerulonephritis in the subject. In one embodiment, the effective amount of the antibody is two doses of 1 gram Obinutuzumab per dose. In some embodiments, Obinutuzumab is administered intravenously. In some embodiment, the two doses of 1 gram per dose of Obinutuzumab are administered about 15 days apart. In some embodiments, a first dose is administered on the same day or split over a period of two days. In an embodiment, the first dose is split over two days wherein 100 mg of Obinutuzumab is administered on day 1 and 900 mg of Obinutuzumab is administered on day 2. In some embodiments, effective amount of the Obinutuzumab is administered to the subject every 6 months, every 1 year, every 18 months, every 2 years, every 3 years, every 4 years, every 5 years, every 10 year, for lifetime of the subject or combinations thereof. In an embodiment, the subject is human.

Also provided herein are methods are treating, inhibiting or reducing severity of glomerulonephritis (GN) in a subject in need thereof comprising, consisting of or consisting essentially of administering an effective amount of an anti-CD20 antibody to the subject, so as to treat, inhibit or reduce the severity of glomerulonephritis in the subject. In one embodiment, the effective amount of the antibody is two doses of 1 gram Obinutuzumab per dose. In some embodiments, Obinutuzumab is administered intravenously. In some embodiment, the two doses of 1 gram per dose of Obinutuzumab are administered about 15 days apart. In some embodiments, a first dose is administered on the same day or split over a period of two days. In an embodiment, the first dose is split over two days wherein 100 mg of Obinutuzumab is administered on day 1 and 900 mg of Obinutuzumab is administered on day 2. In some embodiments, effective amount of the Obinutuzumab is administered to the subject every 6 months, every 1 year, every 18 months, every 2 years, every 3 years, every 4 years, every 5 years, every 10 year, for lifetime of the subject or combinations thereof. In an embodiment, the subject is human.

Also provided herein are methods for desensitizing a subject to antibody mediated transplant rejection (ABMR) in the subject in need thereof. The methods include providing an anti-CD20 antibody (for example, Obinutuzumab) and administering an effective amount of the antibody to the subject so as to desensitize the subject to ABMR. In some embodiments, the subjects are desensitized prior to transplant. In some embodiments, the subjects are desensitized during transplant. In some embodiments, the subjects are desensitized prior to, during and after transplant. In various embodiments, desensitizing the subject includes treating the subject with the anti-CD20 antibody (for example, Obinutuzumab) and Intravenous immunoglobulin (IVIG), with or without plasmapheresis. In various embodiments, the anti-CD20 antibody (for example, Obinutuzumab) and IVIG are administered sequentially. In various embodiments, the anti-CD20 antibody (for example, Obinutuzumab) and IVIG are administered simultaneously. In one embodiment, the effective amount of the antibody is two doses of 1 gram Obinutuzumab per dose. In some embodiments, Obinutuzumab is administered intravenously. In some embodiment, the two doses of 1 gram per dose of Obinutuzumab are administered about 15 days apart. In some embodiments, a first dose is administered on the same day or split over a period of two days. In an embodiment, the first dose is split over two days wherein 100 mg of Obinutuzumab is administered on day 1 and 900 mg of Obinutuzumab is administered on day 2.

Also provided herein are methods for desensitizing a subject to antibody mediated transplant rejection (ABMR) in the subject in need thereof. The methods include administering an effective amount of an anti-CD20 antibody (for example, Obinutuzumab) to the subject so as to desensitize the subject to ABMR. In some embodiments, the subjects are desensitized prior to transplant. In some embodiments, the subjects are desensitized during transplant. In some embodiments, the subjects are desensitized prior to, during and after transplant. In various embodiments, desensitizing the subject includes treating the subject with the anti-CD20 antibody (for example, Obinutuzumab) and Intravenous immunoglobulin (IVIG), with or without plasmapheresis. In various embodiments, the anti-CD20 antibody (for example, Obinutuzumab) and IVIG are administered sequentially. In various embodiments, the anti-CD20 antibody (for example, Obinutuzumab) and IVIG are administered simultaneously. In one embodiment, the effective amount of the antibody is two doses of 1 gram Obinutuzumab per dose. In some embodiments, Obinutuzumab is administered intravenously. In some embodiment, the two doses of 1 gram per dose of Obinutuzumab are administered about 15 days apart. In some embodiments, a first dose is administered on the same day or split over a period of two days. In an embodiment, the first dose is split over two days wherein 100 mg of Obinutuzumab is administered on day 1 and 900 mg of Obinutuzumab is administered on day 2.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 2A-FIG. 2C depict in accordance with various embodiments of the invention, (FIG. 2A) renal biopsy revealing membranous lupus glomerulonephritis; (FIG. 2B) the effect of Rituximab on anti-nuclear antibody (ANA) titers at the time of diagnosis and over 3 years; (FIG. 2C) anti-dsDNA Antibodies at Systemic Lupus Erythematous (SLE) relapse and up to 8 weeks post-treatment

DETAILED DESCRIPTION

Figure 1:
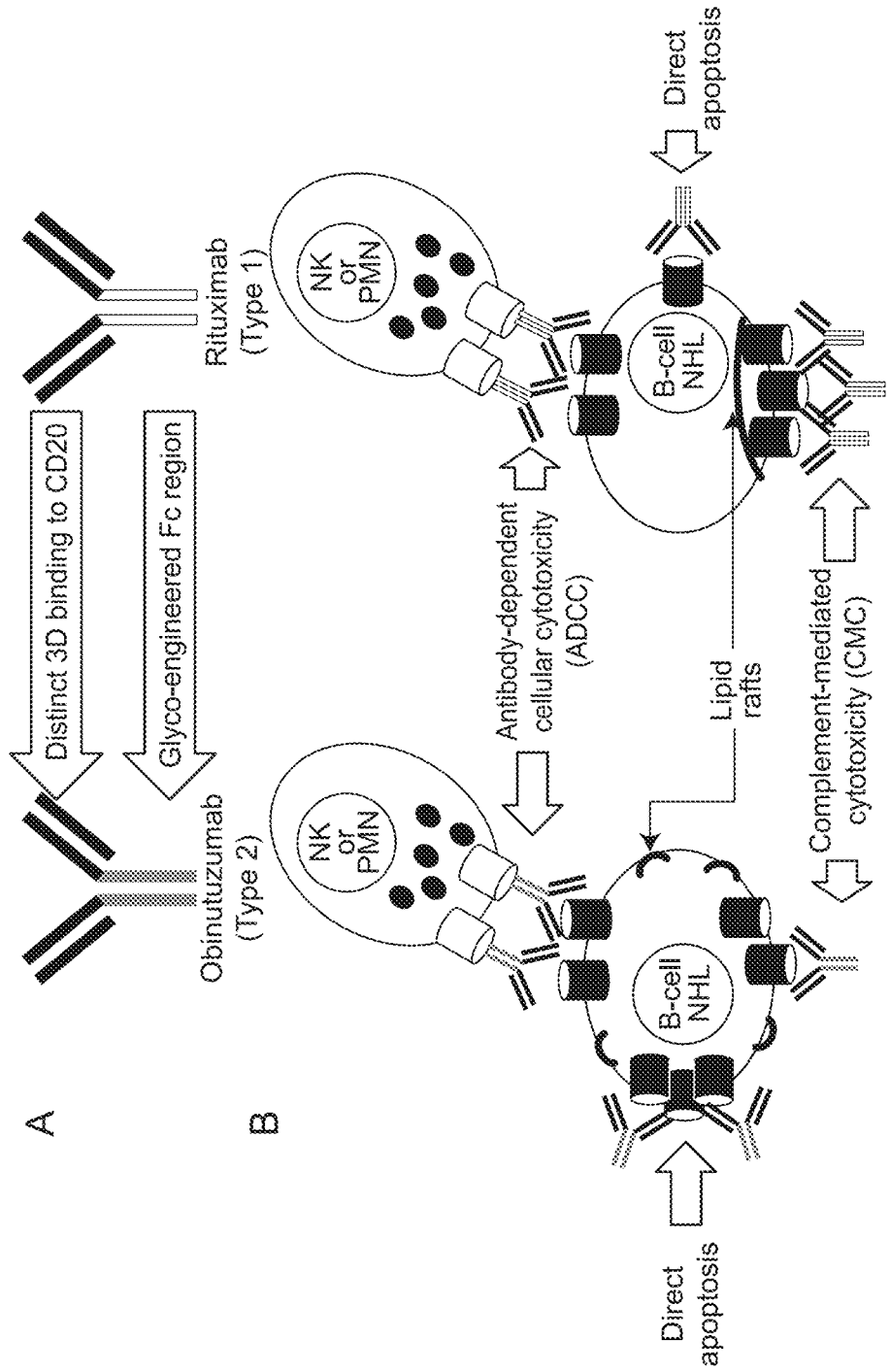
FIG. 1 depicts in accordance with various embodiments of the invention, the mechanism of action of Rituximab (Type 1) versus Obinutuzumab (Type II).

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, NY 2006); Smith, *March's Advanced Organic Chemistry Reactions, Mechanisms and Structure* 7$^{th}$ ed., J. Wiley & Sons (New York, NY 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, NY 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor NY, 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

For references on pediatrics, see Schwartz et al., *The 5-Minute Pediatric Consult* 4$^{th}$ ed., Lippincott Williams & Wilkins, (Jun. 16, 2005); Robertson et al., *The Harriet Lane Handbook: A Manual for Pediatric House Officers* 17$^{th}$ ed., Mosby (Jun. 24, 2005); and Hay et al., *Current Diagnosis and Treatment in Pediatrics* (*Current Pediatrics Diagnosis & Treatment*) 18$^{th}$ ed., McGraw-Hill Medical (Sep. 25, 2006).

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of pancreatic cancer, delay or slowing of nephrotic syndrome, and amelioration or palliation of symptoms associated with nephrotic syndrome.

"Diseases", "conditions" and "disease conditions," as used herein may include, but are in no way limited to any form of nephrotic syndrome.

As used herein, the term "administering," refers to the placement of an agent or a composition as disclosed herein into a subject by a method or route which results in at least partial localization of the agents or composition at a desired site. "Route of administration" may refer to any administration pathway known in the art, including but not limited to oral, topical, aerosol, nasal, via inhalation, anal, intra-anal, peri-anal, transmucosal, transdermal, parenteral, enteral, or local. "Parenteral" refers to a route of administration that is generally associated with injection, including intratumoral, intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intrauterine, intravascular, intravenous, intraarterial, subarachnoid, subcapsular, subcutaneous, transmucosal, or transtracheal. Via the parenteral route, the agent or composition may be in the form of solutions or suspensions for infusion or for injection, or as lyophilized powders. Via the enteral route, the agent or composition can be in the form of capsules, gel capsules, tablets, sugar-coated tablets, syrups, suspensions, solutions, powders, granules, emulsions, microspheres or nanospheres or lipid vesicles or polymer vesicles allowing controlled release. Via the topical route, the agent or composition can be in the form of aerosol, lotion, cream, gel, ointment, suspensions, solutions or emulsions. In an embodiment, agent or composition may be provided in a powder form and mixed with a liquid, such as water, to form a beverage. In accordance with the present invention, "administering" can be self-administering. For example, it is considered as "administering" that a subject consumes a composition as disclosed herein.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In an embodiment, the subject is human. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., nephrotic syndrome) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. For example, a subject can be one who exhibits one or more symptoms for a condition or one or more complications related to the condition or a subject who does not exhibit symptoms. A "subject in need" of diagnosis or treatment for a particular condition can be a subject suspected of having that condition, diagnosed as having that condition, already treated or being treated for that condition, not treated for that condition, or at risk of developing that condition.

A therapeutically or prophylactically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject or the state of the subject prior to administering the anti-CD20 antibody (for example, Obinutuzumab). Measured or measurable parameters include clinically detectable markers of disease, for example, elevated or depressed levels of a biological marker, as well as parameters related to a clinically accepted scale of symptoms or markers for fibrosis and/or inflammation. It will be understood, however, that the total daily usage of the compositions and formulations as disclosed herein will be decided by the attending physician within the scope of sound medical judgment. The exact amount required will vary depending on factors such as the type of disease being treated, gender, age, and weight of the subject.

Provided herein are methods for treating, inhibiting, reducing the severity of and/or delaying progression of nephrotic syndrome in a subject in need thereof. The methods comprise, consist of or consist essentially of providing an anti-CD20 antibody and administering an effective amount of the anti-CD20 antibody to the subject so are to treat, inhibit, reduce the severity of and/or delay progression of nephrotic syndrome in the subject. In some embodiments, the methods comprise, consist of or consist essentially of administering an effective amount of an anti-CD20 antibody to the subject so are to treat, inhibit, reduce the severity of and/or delay progression of nephrotic syndrome in the subject. In one embodiment, nephrotic syndrome is Rituximab-resistant nephrotic syndrome. In one embodiment, the subject is human. In some embodiments, the anti-CD20 antibody is Obinutuzumab, Rituximab or a combination thereof. In one embodiment, the anti-CD20 antibody is Obinutuzumab. In some embodiments, nephrotic syndrome in the subject is caused by any one or more of minimal change disease, focal sclerosis syndrome, membranous glomerulonephritis, IgA nephropathy and cryoglobulinemic glomerulonephritis. In various embodiments, the anti-CD20 antibody or a fragment thereof described herein is administered to the subject before, during, or after the subject develops the nephrotic syndrome. In some embodiments, the anti-CD20 antibody or a fragment thereof is administered to the subject 1-3 times per day or 1-7 times per week. In some embodiments, the anti-CD20 antibody or a fragment thereof is administered to the subject for 1-5 days, 1-5 weeks, 1-5 months, 1-5 years, 5-10 years or for lifetime of the subject. In some embodiments, the subject has been administered standard-of-care treatment for nephrotic syndrome prior to administration of the anti-CD20 antibody (for example, prior to administration of Obinutuzumab). In some embodiments, the subject does not respond to or poorly responds to standard-of-care treatment for nephrotic syndrome prior to administration of anti-CD20 antibody (for example, Obinutuzumab). In some embodiments, the subject has not been administered standard-of-care treatment for nephrotic syndrome prior to administration of anti-CD20 antibody (for example, Obinutuzumab). In some embodiments, the standard-of-care treatment for nephrotic syndrome is administered simultaneously or sequentially with the anti-CD20 antibody (for example, Obinutuzumab). In exemplary embodiments, the standard-of-care treatment for nephrotic syndrome is steroid, CELLCEPT®, cyclophosphamide, cyclosporine, tacrolimus and Rituximab. Nephrotic syndrome treatments include high dose prednisone (steroids), mycophenolic acid (CELLCEPT®) and occasionally calcineurin inhibitors (cyclosporine and tacrolimus). All are used in various combinations. In addition, high doses of Cytoxan are used in severe cases. Cytoxan has a high side effect profile and is not used routinely.

Also provided herein are methods for treating, inhibiting, reducing the severity of and/or delaying progression of glomerulonephritis (GN) in a subject in need thereof. The methods comprise, consist of or consist essentially of providing an anti-CD20 antibody and administering an effective amount of the anti-CD20 antibody to the subject so are to treat, inhibit, reduce the severity of and/or delay progression of glomerulonephritis in the subject.

In some embodiments, the methods comprise, consist of or consist essentially of administering an effective amount an anti-CD20 antibody to the subject so are to treat, inhibit, reduce the severity of and/or delay progression of glomerulonephritis in the subject. In some embodiments, glomerulonephritis is membranous glomerulonephritis, cryoglobulinemic glomerulonephritis, IgA nephropathy, minimal change disease, focal segmental glomerulosclerosis, recurrent nephritis, nephrotic syndrome after kidney transplantation and transplant glomerulopathy with proteinuria and nephrotic syndrome in kidney transplant patients. In one embodiment, the subject is human. In some embodiments, the anti-CD20 antibody is Obinutuzumab, Rituximab or a combination thereof. In one embodiment, the anti-CD20 antibody is Obinutuzumab. In various embodiments, the anti-CD20 antibody or a fragment thereof described herein is administered to the subject before, during, or after the subject develops glomerulonephritis. In some embodiments, the anti-CD20 antibody or a fragment thereof is administered to the subject 1-3 times per day or 1-7 times per week. In some embodiments, the anti-CD20 antibody or a fragment thereof is administered to the subject for 1-5 days, 1-5 weeks, 1-5 months, 1-5 years, 5-10 years or for lifetime of the subject. In some embodiments, the subject has been administered standard-of-care treatment for glomerulonephritis prior to administration of the anti-CD20 antibody (for example, prior to administration of Obinutuzumab). In some embodiments, the subject does not respond to or poorly responds to standard-of-care treatment for glomerulonephritis prior to administration of anti-CD20 antibody (for example, Obinutuzumab). In some embodiments, the subject has not been administered standard-of-care treatment for glomerulonephritis prior to administration of anti-CD20 antibody (for example, Obinutuzumab). In some embodiments, the standard-of-care treatment for glomerulonephritis is administered simultaneously or sequentially with the anti-CD20 antibody (for example, Obinutuzumab). In exemplary embodiments, the standard-of-care treatment for glomerulonephritis includes high dose prednisone (steroids), mycophenolic acid (CELLCEPT®), plasmapheresis and/or Rituximab. All are used in various combinations.

Further provided herein is a method for treating, inhibiting, reducing the severity of and/or delaying progression of Rituximab-resistant nephrotic syndrome. The methods comprise, consist of or consist essentially of providing an anti-CD20 antibody and administering an effective amount of the anti-CD20 antibody to the subject so are to treat, inhibit, reduce the severity of and/or delay progression of Rituximab-resistant nephrotic syndrome in the subject. In some embodiments, the methods comprise, consist of or consist essentially of administering an effective amount of an anti-CD20 antibody to the subject so are to treat, inhibit, reduce the severity of and/or delay progression of Rituximab-resistant nephrotic syndrome in the subject. In one embodiment, the subject is human. In one embodiment, the anti-CD20 antibody is Obinutuzumab. In various embodiments, the anti-CD20 antibody or a fragment thereof described herein is administered to the subject before, during, or after the subject develops Rituximab-resistant nephrotic syndrome. In some embodiments, the anti-CD20 antibody or a fragment thereof is administered to the subject 1-3 times per day or 1-7 times per week. In some embodiments, the anti-CD20 antibody or a fragment thereof is administered to the subject for 1-5 days, 1-5 weeks, 1-5 months, 1-5 years, 5-10 years or for lifetime of the subject. In some embodiments, the subject has been administered Rituximab and does not respond to or responds poorly to Rituximab.

Also provided herein is a method for treating, inhibiting, reducing the severity of and/or delaying progression of membranous glomerulonephritis. The methods comprise, consist of or consist essentially of providing an anti-CD20 antibody and administering an effective amount of the anti-CD20 antibody to the subject so are to treat, inhibit, reduce the severity of and/or delay progression of membranous glomerulonephritis in the subject. In some embodiments, the methods comprise, consist of or consist essentially of administering an effective amount of an anti-CD20 antibody to the subject so are to treat, inhibit, reduce the severity of and/or delay progression of membranous glomerulonephritis in the subject. In one embodiment, the subject is human. In some embodiments, the anti-CD20 antibody is Obinutuzumab, Rituximab or a combination thereof. In one embodiment, the anti-CD20 antibody is Obinutuzumab. In various embodiments, the anti-CD20 antibody or a fragment thereof described herein is administered to the subject before, during, or after the subject develops membranous glomerulonephritis. In some embodiments, the anti-CD20 antibody or a fragment thereof is administrated to the subject 1-3 times per day or 1-7 times per week. In some embodiments, the anti-CD20 antibody or a fragment thereof is administered to the subject for 1-5 days, 1-5 weeks, 1-5 months, 1-5 years, 5-10 years or for lifetime of the subject. In some embodiments, the subject has been administered standard-of-care treatment for membranous glomerulonephritis prior to administration of the anti-CD20 antibody (for example, prior to administration of Obinutuzumab). In some embodiments, the subject does not respond to or poorly responds to standard-of-care treatment for membranous glomerulonephritis prior to administration of anti-CD20 antibody (for example, Obinutuzumab). In some embodiments, the subject has not been administered standard-of-care treatment for membranous glomerulonephritis prior to administration of anti-CD20 antibody (for example, Obinutuzumab). In some embodiments, the standard-of-care treatment for membranous glomerulonephritis is administered simultaneously or sequentially with the anti-CD20 antibody (for example, Obinutuzumab). In exemplary embodiments, the standard-of-care treatment for membranous glomerulonephritis is high dose prednisone (steroids), mycophenolic acid (CELLCEPT®), plasmapheresis and/or Rituximab. All are used in various combinations.

Further provided herein is a method for treating, inhibiting, reducing the severity of and/or delaying progression of cryoglobulinemic glomerulonephritis (CGN). The methods comprise, consist of or consist essentially of providing an anti-CD20 antibody and administering an effective amount of the anti-CD20 antibody to the subject so are to treat, inhibit, reduce the severity of and/or delay progression of cryoglobulinemics glomerulonephritis in the subject. In some embodiments, the methods comprise, consist of or consist essentially of administering an effective amount of an anti-CD20 antibody to the subject so are to treat, inhibit, reduce the severity of and/or delay progression of cryoglobulinemic glomerulonephritis in the subject. In one embodiment, the subject is human. In some embodiments, the anti-CD20 antibody is Obinutuzumab, Rituximab or a combination thereof. In one embodiment, the anti-CD20 antibody is Obinutuzumab. In various embodiments, the anti-CD20 antibody or a fragment thereof described herein is administered to the subject before, during, or after the subject develops cryoglobulinemic glomerulonephritis. In some embodiments, the anti-CD20 antibody or a fragment thereof is administered to the subject 1-3 times per day or 1-7 times per week. In some embodiments, the anti-CD20 antibody or a fragment thereof is administered to the subject for 1-5 days, 1-5 weeks, 1-5 months, 1-5 years, 5-10 years or for lifetime of the subject. In some embodiments, the subject has been administered standard-of-care treatment for cryoglobulinemic glomerulonephritis prior to administration of the anti-CD20 antibody (for example, prior to administration of Obinutuzumab). In some embodiments, the subject does not respond to or poorly responds to standard-of-care treatment for cryoglobulinemic glomerulonephritis prior to administration of anti-CD20 antibody (for example, Obinutuzumab). In some embodiments, the subject has not been administered standard-of-care treatment for cryoglobulinemic glomerulonephritis prior to administration of anti-CD20 antibody (for example, Obinutuzumab). In some embodiments, the standard-of-care treatment for cryoglobulinemic glomerulonephritis is administered simultaneously or sequentially with the anti-CD20 antibody (for example, Obinutuzumab). In exemplary embodiments, the standard-of-care treatment for cryoglobulinemic glomerulonephritis includes high dose prednisone (steroids), mycophenolic acid (CELLCEPT®), plasmapheresis and/or Rituximab. All are used in various combinations. Many patients with CGN also have hepatitis C or B and may be at risk for progression of liver failure if excessive immunosuppression is used. Newer anti-hepatitis C therapies have not altered the course of CGN. Because of this, and the relative inefficacy of many of the drugs, there is a large unmet need for new therapies that are less toxic in patients with CGN.

Also provided herein is a method for treating, inhibiting, reducing the severity of and/or delaying progression of IgA nephropathy (IgAN). The methods comprise, consist of or consist essentially of providing an anti-CD20 antibody and administering an effective amount of the anti-CD20 antibody to the subject so are to treat, inhibit, reduce the severity of and/or delay progression of IgA nephropathy in the subject. In some embodiments, the methods comprise, consist of or consist essentially of administering an effective amount an anti-CD20 antibody to the subject so are to treat, inhibit, reduce the severity of and/or delay progression of IgA nephropathy in the subject. In one embodiment, the subject is human. In some embodiments, the anti-CD20 antibody is Obinutuzumab, Rituximab or a combination thereof. In one embodiment, the anti-CD20 antibody is Obinutuzumab. In various embodiments, the anti-CD20 antibody or a fragment thereof described herein is administered to the subject before, during, or after the subject develops IgA nephropathy. In some embodiments, the anti-CD20 antibody or a fragment thereof is administered to the subject 1-3 times per day or 1-7 times per week. In some embodiments, the anti-CD20 antibody or a fragment thereof is administered to the subject for 1-5 days, 1-5 weeks, 1-5 months, 1-5 years, 5-10 years or for lifetime of the subject. In some embodiments, the subject has been administered standard-of-care treatment for IgA nephropathy prior to administration of the anti-CD20 antibody (for example, prior to administration of Obinutuzumab). In some embodiments, the subject does not respond to or poorly responds to standard-of-care treatment for IgA nephropathy prior to administration of anti-CD20 antibody (for example, Obinutuzumab). In some embodiments, the subject has not been administered standard-of-care treatment for IgA nephropathy prior to administration of anti-CD20 antibody (for example, Obinutuzumab). In some embodiments, the standard-of-care treatment for IgA nephropathy is administered simultaneously or sequentially with the anti-CD20 antibody (for example, Obinutuzumab). In exemplary embodiments, the standard-of-care treatment for IgA nephropathy is high dose steroid, mycophenolate mofetil, angiotensin-converting enzyme inhibitor (ACEI) or angtiotensin receptor blocker (ARB), fish oil, azathioprine, and cyclophosphamide. Most patients with IGAN have mild to moderate disease, and can be controlled with ACEI/ARB therapy without immunosuppression. However, a sizeable number do have more aggressive disease and progress to renal failure. Currently there are no approved drugs for treating IgAN. Inventors' work has shown resolution of clinical and laboratory features of IgAN with Rituximab and CELLCEPT®, supporting the use of Obi therapy to treat IgAN especially since IgAN is an autoimmune disease.

Also provided herein are methods for treating, inhibiting or reducing severity of nephrotic syndrome in a subject in need thereof comprising providing an anti-CD20 antibody and administering an effective amount of the anti-CD20 antibody to the subject, so as to treat, inhibit or reduce the severity of nephrotic syndrome in the subject. In one embodiment, the effective amount of the antibody is two doses of 1 gram Obinutuzumab per dose. In some embodiments, Obinutuzumab is administered intravenously. In some embodiment, the two doses of 1 gram per dose of Obinutuzumab are administered about 15 days apart. In some embodiments, a first dose is administered on the same day or split over a period of two days. In an embodiment, the first dose is split over two days wherein 100 mg of Obinutuzumab is administered on day 1 and 900 mg of Obinutuzumab is administered on day 2. In some embodiments, effective amount of the Obinutuzumab is administered to the subject every 6 months, every 1 year, every 18 months, every 2 years, every 3 years, every 4 years, every 5 years or combinations thereof. In an embodiment, the subject is human.

Also provided herein are methods for treating, inhibiting or reducing severity of nephrotic syndrome in a subject in need thereof comprising administering an effective amount of an anti-CD20 antibody to the subject, so as to treat, inhibit or reduce the severity of nephrotic syndrome in the subject. In one embodiment, the effective amount of the antibody is two doses of 1 gram Obinutuzumab per dose. In some embodiments, Obinutuzumab is administered intravenously. In some embodiment, the two doses of 1 gram per dose of Obinutuzumab are administered about 15 days apart. In some embodiments, a first dose is administered on the same day or split over a period of two days. In an embodiment, the first dose is split over two days wherein 100 mg of Obinutuzumab is administered on day 1 and 900 mg of Obinutuzumab is administered on day 2. In some embodiments, effective amount of the Obinutuzumab is administered to the subject every 6 months, every 1 year, every 18 months, every 2 years, every 3 years, every 4 years, every 5 years or combinations thereof. In an embodiment, the subject is human.

Further provided herein are methods are treating, inhibiting or reducing severity of glomerulonephritis (GN) in a subject in need thereof comprising providing an anti-CD20 antibody and administering an effective amount of the antibody to the subject, so as to treat, inhibit or reduce the severity of glomerulonephritis in the subject. In one embodiment, the effective amount of the antibody is two doses of 1 gram Obinutuzumab per dose. In some embodiments, Obinutuzumab is administered intravenously. In some embodiment, the two doses of 1 gram per dose of Obinutuzumab are administered about 15 days apart. In some embodiments, a first dose is administered on the same day or split over a period of two days. In an embodiment, the first dose is split over two days wherein 100 mg of Obinutuzumab is administered on day 1 and 900 mg of Obinutuzumab is administered on day 2. In some embodiments, effective amount of the Obinutuzumab is administered to the subject every 6 months, every 1 year, every 18 months, every 2 years, every 3 years, every 4 years, every 5 years or combinations thereof. In an embodiment, the subject is human.

Also provided herein are methods are treating, inhibiting or reducing severity of glomerulonephritis (GN) in a subject in need thereof comprising administering an effective amount of an anti-CD20 antibody to the subject, so as to treat, inhibit or reduce the severity of glomerulonephritis in the subject. In one embodiment, the effective amount of the antibody is two doses of 1 gram Obinutuzumab per dose. In some embodiments, Obinutuzumab is administered intravenously. In some embodiment, the two doses of 1 gram per dose of Obinutuzumab are administered about 15 days apart. In some embodiments, a first dose is administered on the same day or split over a period of two days. In an embodiment, the first dose is split over two days wherein 100 mg of Obinutuzumab is administered on day 1 and 900 mg of Obinutuzumab is administered on day 2. In some embodiments, effective amount of the Obinutuzumab is administered to the subject every 6 months, every 1 year, every 18 months, every 2 years, every 3 years, every 4 years, every 5 years or combinations thereof. In an embodiment, the subject is human.

Also provided herein are methods for desensitizing a subject to antibody mediated transplant rejection (ABMR) in the subject in need thereof. The methods include providing an anti-CD20 antibody (for example, Obinutuzumab) and administering an effective amount of the antibody to the subject so as to desensitize the subject to ABMR. In some embodiments, the subjects are desensitized prior to transplant. In some embodiments, the subjects are desensitized during transplant. In some embodiments, the subjects are desensitized prior to, during and after transplant. In various embodiments, desensitizing the subject includes treating the subject with the anti-CD20 antibody (for example, Obinutuzumab) and Intravenous Gammaglobulin (IVIG), with or without plasmapheresis. In various embodiments, the anti-CD20 antibody (for example, Obinutuzumab) and IVIG are administered sequentially. In various embodiments, the anti-CD20 antibody (for example, Obinutuzumab) and IVIG are administered simultaneously. In one embodiment, the effective amount of the antibody is two doses of 1 gram Obinutuzumab per dose. In some embodiments, Obinutuzumab is administered intravenously. In some embodiment, the two doses of 1 gram per dose of Obinutuzumab are administered about 15 days apart. In some embodiments, a first dose is administered on the same day or split over a period of two days. In an embodiment, the first dose is split over two days wherein 100 mg of Obinutuzumab is administered on day 1 and 900 mg of Obinutuzumab is administered on day 2. The effective amount of IVIG will be apparent to a person of skill in the art.

Also provided herein are methods for desensitizing a subject to antibody mediated transplant rejection (ABMR) in the subject in need thereof. The methods include administering an effective amount of an anti-CD20 antibody (for example, Obinutuzumab) to the subject so as to desensitize the subject to ABMR. In some embodiments, the subjects are desensitized prior to transplant. In some embodiments, the subjects are desensitized during transplant. In some embodiments, the subjects are desensitized prior to, during and after transplant. In various embodiments, desensitizing the subject includes treating the subject with the anti-CD20 antibody (for example, Obinutuzumab) and Intravenous Gammaglobulin (IVIG), with or without plasmapheresis. In various embodiments, the anti-CD20 antibody (for example, Obinutuzumab) and IVIG are administered sequentially. In various embodiments, the anti-CD20 antibody (for example, Obinutuzumab) and IVIG are administered simultaneously. In one embodiment, the effective amount of the antibody is two doses of 1 gram Obinutuzumab per dose. In some embodiments, Obinutuzumab is administered intravenously. In some embodiment, the two doses of 1 gram per dose of Obinutuzumab are administered about 15 days apart. In some embodiments, a first dose is administered on the same day or split over a period of two days. In an embodiment, the first dose is split over two days wherein 100 mg of Obinutuzumab is administered on day 1 and 900 mg of Obinutuzumab is administered on day 2. The effective amount of IVIG will be apparent to a person of skill in the art.

Dosages

In some embodiments of the invention, the effective amounts of the anti-CD20 antibody (for example, Obinutuzumab) can be in the range of about 10-50 mg/day, 50-100 mg/day, 100-150 mg/day, 150-200 mg/day, 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day, 1900-2000 mg/day, 2000-2100 mg/day, 2100-2200 mg/day, 2200-2300 mg/day, 2300-2400 mg/day, 2400-2500 mg/day, 2500-2600 mg/day, 2600-2700 mg/day, 2700-2800 mg/day, 2800-2900 mg/day or 2900-3000 mg/day. In one embodiment the anti-CD20 antibody is Obinutuzumab.

In further embodiments of the invention, the effective amount of the anti-CD20 antibody (including Obinutuzumab) for use with the claimed methods may be in the range of 1-5 mg/kg, 5-10 mg/kg, 10-50 mg/kg, 50-100 mg/kg, 100-150 mg/kg, 150-200 mg/kg, 100-200 mg/kg, 200-300 mg/kg, 300-400 mg/kg, 400-500 mg/kg, 500-600 mg/kg, 600-700 mg/kg, 700-800 mg/kg, 800-900 mg/kg or 900-1000 mg/kg. In one embodiment the anti-CD20 antibody is Obinutuzumab. In one embodiment, the effective amount of Obinutuzumab is 2 doses of 1 gram Obinutuzumab (1 g×2). The second dose may be administered, for example, 1-3, 1-5, 1-10, 5-10, 10-15, 11-15, 12-15, 13-15, 14-15 or 15-20 days after the first dose. The first dose may be infused over a period of 2 days; on the first day 100 mg may be infused at 25 mg/hr×4 hours and on the second day, 900 mg may be infused at 50 mg/hr and increased every 30 minutes to a maximum rate of 400 mg/hr. The second dose (for example, administered day 15) of 1000 mg may start at 100 mg/hr and increased 100 mg/hr increments every 30 minutes to a maximum of 400 mg/hr.

Typical dosages of an effective amount of anti-CD20 antibody, such as Obinutuzumab, can be in the ranges recommended by the manufacturer where known therapeutic compounds are used, and also as indicated to the skilled artisan by the in vitro responses or responses in animal models. For example, Obinutuzumab is currently recommended for the treatment of chronic lymphocytic anemia as administering 100 mg on day 1, 900 mg on day 2 and 1000 mg on day 8, and day 15. The same or similar dosing can be used in accordance with various embodiments of the present invention, or an alternate dosage may be used in connection with alternate embodiments of the invention. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models For treatment of nephrotic syndrome, Obinutuzumab (for example, 1 g) may be given every 13-15 days for a total of 2 doses. The first dose may be split over 2 days: 100 mg on day 1 and 900 mg on day 2, however the full 1 g may be infused, for example, once the package insert for Obinutuzumab is updated. The $2^{nd}$ dose may be infused at a rate of 100 mg/hr and increased by 100 mg/hr increments every 30 minutes to a maximum of 400 mg/hr. Package labeling updates may be published over time to also accommodate faster infusion rates. Repeat doses may be administered per clinical response after a dose response period of at least 2 weeks.

Pharmaceutical Composition

In various embodiments, the present invention provides a pharmaceutical composition. The pharmaceutical composition includes an anti-CD20 antibody (for example, Obinutuzumab). The pharmaceutical compositions according to the invention can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal, parenteral or enteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the parenteral route, the compositions may be in the form of solutions or suspensions for infusion or for injection. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Typically, the compositions are administered by injection. Methods for these administrations are known to one skilled in the art.

The pharmaceutical compositions according to the invention can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Before administration to patients, formulants may be added to the rAAV vector, the cell transfected with the rAAV vector, or the supernatant conditioned with the transfected cell. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxyethyl starch and carboxymethylcellulose, or mixtures thereof. "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

In some embodiments, polymers as formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

Kits

In various embodiments, the present invention provides a kit for treating or inhibiting nephrotic syndrome. The kit is an assemblage of materials or components, including an anti-CD20 antibody. Thus in some embodiments, the kit contains Obinutuzumab.

The exact nature of the components configured in the inventive kit depends on its intended purpose. In one embodiment, the kit is configured particularly for human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat or inhibit nephrotic syndrome in a subject. Optionally, the kit also contains other useful components, such as, measuring tools, diluents, buffers, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a bottle used to contain suitable quantities of an inventive composition containing anti-CD20 antibody, such as Obinutuzumab. The packaging material generally has an external label which indicates the contents and/or purpose of the kit and/or its components.

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

Example 1

FIG. 1 describes the differences in mechanism of action between Rituximab and Obinutuzumab (Obi). This figure shows the differences between Type I and Type II anti-CD20 molecules. Type 1 molecules bind to CD20 localized in lipid rafts on B-cells. This can result in incomplete B-cell depletion due to endocytosis of the CD20/anti-CD20 complex. Type 1 anti-CD20 depletes primarily through complement dependent cytotoxicity with low antibody-dependent cell-mediated cytotoxicity (ADCC). However, the glyco-engineered Obinutuzumab has much stronger affinity for the low affinity immunoglobulin gamma Fc region receptor III-A (FcgRIIIa) and results in enhanced depletion of B-cells through ADCC. Obinutuzumab has approximately 5-50-fold greater potency for depletion in ADCC compared to Rituximab. Obinutuzumab also kills B-cells directly through a mechanism known as homotypic aggregation. Overall, clinical studies in B-cell malignancies have shown superior B-cell depletion in peripheral blood, spleen and lymph nodes of patients treated with Obinutuzumab versus Rituximab.

For treatment of nephrotic syndrome, 1 gram (g) of Obinutuzumab may be administered every 15 days for a total of 2 doses. The first dose may be split over 2 days: 100 mg on day 1 and 900 mg on day 2. However the full 1 g of Obinutuzumab may be infused (for example, once the package insert is updated). The $2^{nd}$ dose may be infused at a rate of 100 mg/hr and increased by 100 mg/hr increments every 30 minutes to a maximum of 400 mg/hr.

Figure 2A:
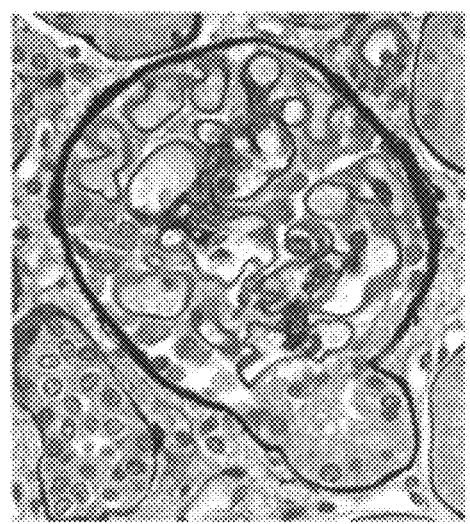
Figure 2A:
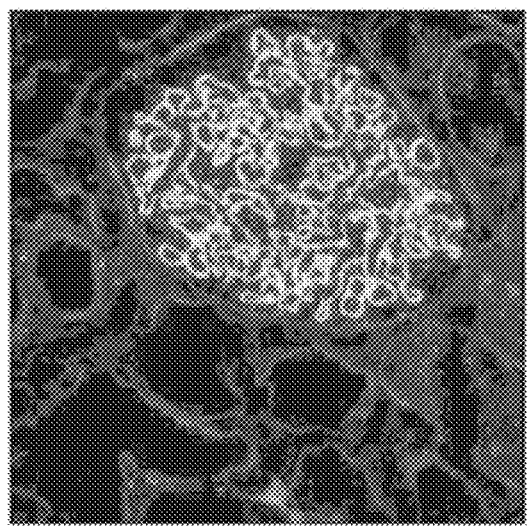
Figure 2A:
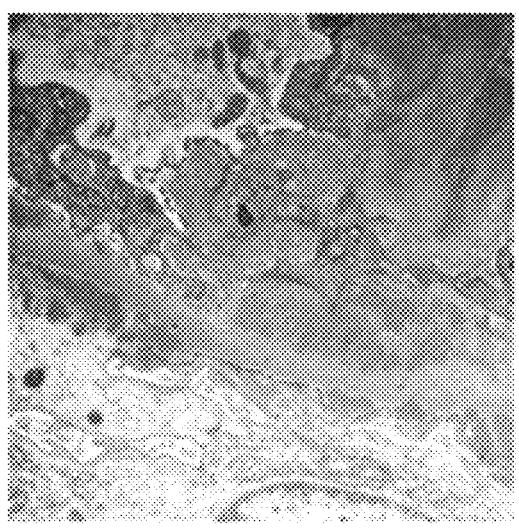

As shown in FIG. 2A and FIG. 2B: Case Presentation—A 31 year old African American male with systemic lupus erythematosus (SLE) presented with nephrotic syndrome, acute renal failure (ARF) and arthralgia with right costovertebral angle (CVA) tenderness. The patient's Albumin level was 0.6 g/dl (normal range is 3.5-5 g/dl) on admission with 10 g proteinuria (normal is <1 g). The patient's auto-antibody levels were: positive for Anti-Nuclear antibody (ANA) with the antibody titer of 1:640 (normal is <1:40 antibody titer); anti-ds DNA was initially negative (normal<1:10 titer) and then increased to 1:640; complement C3 was 40 mg/dl (normal is 79-152 mg/dl), and complement C4 was 11 mg/dl (normal is 16-38 mg/dl). A computerized tomography (CT) scan of chest revealed R pulmonary embolism. Biopsy showed membranous lupus nephritis (see FIG. 2A). Treatment: the patient received high-dose steroids with taper. The patient received two doses of 1 g Rituximab and 750 mg bid (twice a day) of mycophenolate mofetil (CELLCEPT®). Results: At 2 weeks post-Rituximab patient developed complete remission for 3 years. ANA nadir was 1:320. The patient had an initial remission, but relapsed 3 years later. The ANA titers were not well controlled with Rituximab therapy. (see FIG. 2B).

As shown in FIG. 2C, Case Follow Up: The above patient again presented with similar symptoms and weight loss and right CVA tenderness were again noted. The patient also complained of hemoptysis. Right pulmonary embolism was diagnosed. The patient also had ANA 1:640 (normal titer is <1:40) and now anti-dsDNA was 1:640 (normal titer is <1:10). The patient was treated in a similar manner; however, the patient received Obinutuzumab instead of Rituximab and excellent clinical response was seen. Specifically, the patient received 2 doses of 1 gram Obi intravenously (IV) and each dose was separated by 15 days. The first dose was split over 2 days. One week after the first dose of 1 gram Obinutuzumab, the anti-ds-DNA titer was decreased to 1:40 and two months after the second dose of 1 gram Obinutuzumab, the anti-ds-DNA titer decreased to 1:20. This is a powerful demonstration of the efficacy of Obinutuzumab in promoting a rapid remission of SLE.

Figure 3:
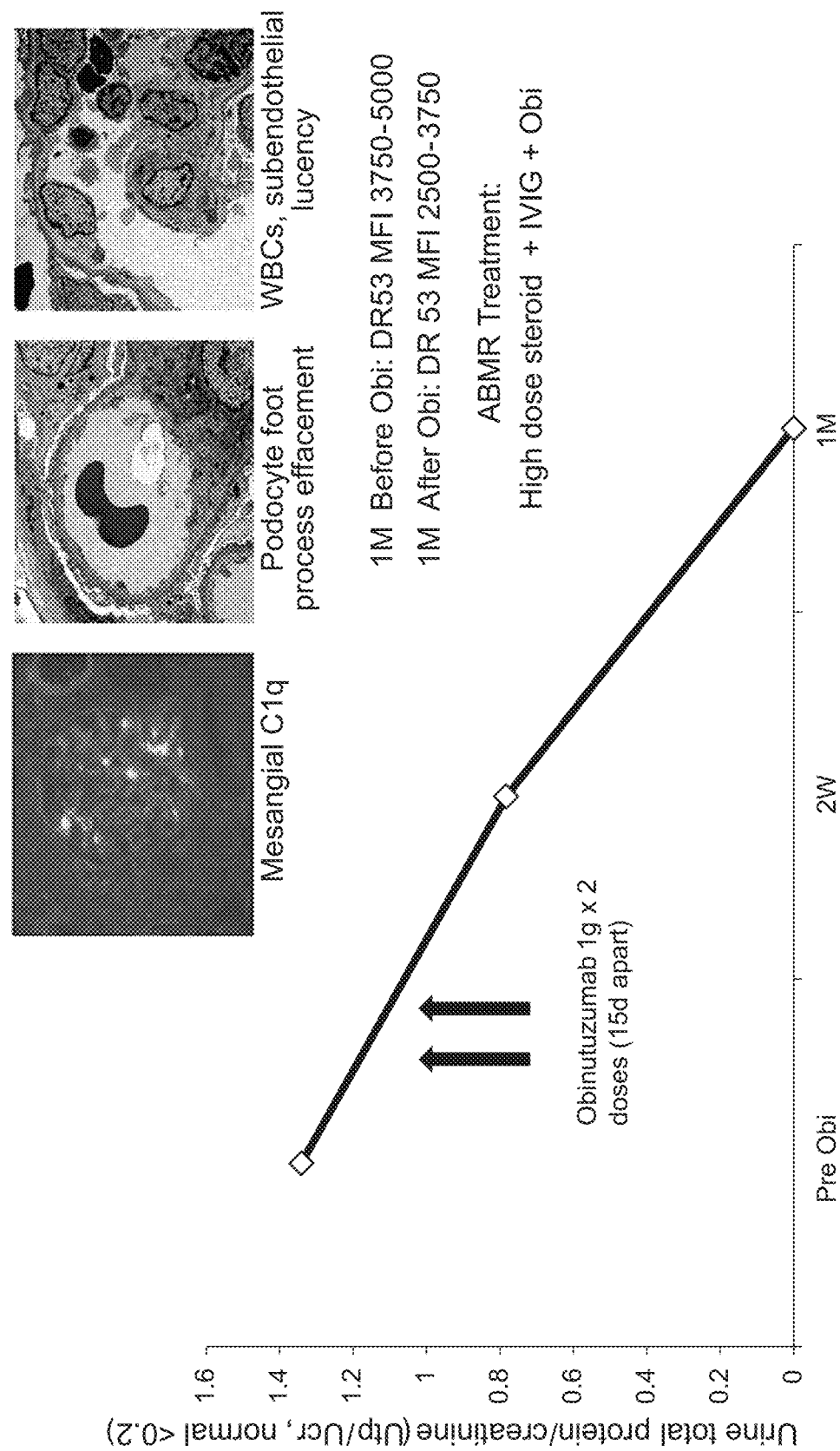
FIG. 3 depicts in accordance with various embodiments of the invention, the effect of Obi in a patient with recurrence of focal segmental glomerulosclerosis (FSGS) and with antibody mediated rejection (ABMR).

The patient shown in FIG. 3 is a 39 year old Asian American female who received kidney transplant from her brother in 2011. The patient had recurrence of focal segmental glomerulosclerosis (FSGS) in her allograft and was not responsive to Rituximab therapy. She also had antibody mediated rejection (ABMR). The patient received 2 doses of 1 g Obinutuzumab intravenously and each dose was separated by 15 days. The first dose was split over 2 days. One month after the 2 doses of Obinutuzumab, the patient's proteinuria (decreased urine total protein/creatinine ratio, UTP/Cr) and renal dysfunction had completely resolved, further supporting the use of Obinutuzumab in treatment of nephrotic syndrome.

Figure 4:
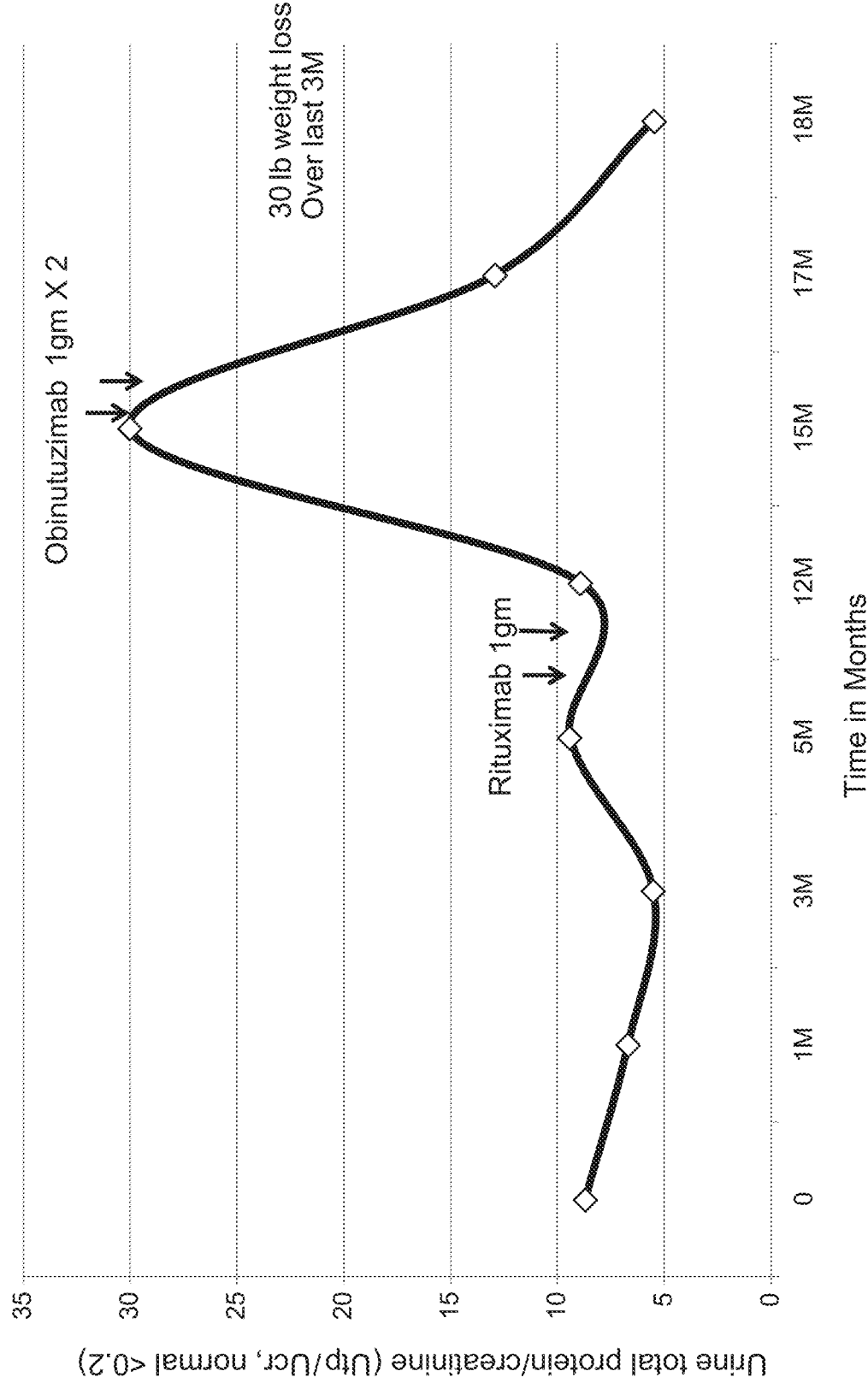
FIG. 4 depicts in accordance with various embodiments of the invention, the effect of Obi in a patient with drug- and Rituximab-resistant minimal change disease nephrotic syndrome (NS).

FIG. 4 shows the course of a 65 year old patient with Rituximab-resistance (also known as drug resistant NS or steroid resistant NS) nephrotic syndrome due to minimal change disease after administration of steroids or Rituximab. The patient was uncontrolled for several years. The patient received two doses of 1 g Obinutuzumab per dose intravenously; the first dose was split over two days and the second dose was administered 15 days later. After the above treatment, the patient lost 30 lbs of mainly water weight which presented as edema and showed resolution of proteinuria marked by decrease in UTP/Cr ratio.

Example 2

There is extensive data with Rituximab (RTX, Type I anti-CD20) for desensitization (DES) and treatment of ABMR. There is also a comparable data in treatment of glomerulonephritis (GN) and nephrotic syndrome (NS). However, Rituximab may not always be effective. The inventors report on the use of Obinutuzumab in GN and human leukocyte antigen (HLA) sensitized patients and show that Obinutuzumab is more effective in depletion of B-cells than Rituximab.

Methods: We identified 11 patients with primary GN and NS, patients with recurrent GN and NS post-transplant and patients with RTX-resistant DES and ABMR who were subsequently treated with Obinutuzumab. Obinutuzumab was administered on day 1 (100 mg), day 2 (900 mg) and day 15 (1000 mg) as per chronic lymphocytic leukemia (CLL) dosing guidelines. Pre-medication with acetaminophen 650 mg by mouth (p.o.), diphenhydramine 25 mg p.o. and methylprednisolone 40 mg intravenously (i.v) were given. Patients were monitored for relevant clinical and laboratory parameters specific to their condition. These included: donor specific antibody (DSAs) (pre and 1 month (M) post-treatment), autoantibodies (anti-dsDNA and anti-AT1R) pre and 1 month post-treatment, serum creatinine (SCr) and degrees of proteinuria.

Results: From a safety standpoint, Obinutuzumab was very well tolerated in this non-B-cell malignancy population. No infusion adverse event/significant adverse event (AE/SAE) was noted. One patient developed *Clostridium difficile* (*C. diff*) diarrhea 1 month post-Obinutuzumab, which resolved. The details of responses to OBI treatment are shown in Table 1.

TABLE 1

Obinutuzumab use in drug resistant GN and ABMR. Relative intensity scale (RIS) [0 point = No DSA; 2 points = <5000 mean fluoresce intensity {weak}; 5 points = 5000-10000 MFI {moderate}; 10 points = >10,000 {strong}.

|  | SCr (mg/dl) | | UTP/Cr | | Antibodies | |
| --- | --- | --- | --- | --- | --- | --- |
| N = 11 | Pre | Post | Pre | Post | Pre | Post |
| Primary Glomerular Disease (n = 2) | | | | | | |
| SLE relapse | 1.1 | 0.8 | 8.7 | 0.83 | 640 | 20 |
| Minimal change disease (MCD-1) | 1.1 | 0.9 | 8.9 | 5.58 | — | — |
| MCD-2 | 1.5 | 0.9 | 18.2 | 5.2 | — | — |
| Recurrent GN post kidney transplant (n = 5) | | | | | | |
| Membranous GN (MGN) | 1.7 | 1.92 | 4.68 | 0.95 | — | — |
| FSGS-1 | 2.1 | 2 | 2.4 | 2 | — | — |
| FSGS-2 | 1.6 | 1.3 | 3.94 | 3.41 | — | — |
| FSGS | 0.9 | 0.9 | 1.3 | 0 | — | — |
| Desensitization (n = 1) | | | | | | |
| AT1R antibody strong | 5.1(Pre-Tx) | 0.9 | — | — | AT1Rab 40 | AT1Rab 11 |

TABLE 1-continued

Obinutuzumab use in drug resistant GN and ABMR. Relative intensity scale (RIS) [0 point = No DSA; 2 points = <5000 mean fluoresce intensity {weak}; 5 points = 5000-10000 MFI {moderate}; 10 points = >10,000 {strong}.

| N = 11 | SCr (mg/dl) | | UTP/Cr | | Antibodies | |
|---|---|---|---|---|---|---|
| | Pre | Post | Pre | Post | Pre | Post |
| ABMR post kidney transplant (n = 3) | | | | | | |
| Bx Proven ABMR and FSGS recurrence | 0.9 | 0.9 | 84.1 | <6 | DR53 MFI 3750-5000 | DR53 2500-3750 |
| BX proven ABMR, s/p PLEX + I + R, Anti-IL6R antibody | 1.8 | 1.95 | — | — | DQ8 RIS 5 | n/a |
| BX proven Acute ABMR s/p PLEX + IVIG | 1.1 | 1.2 | — | — | Multiple DSA RIS: 47 | Multiple DSA RIS: 27 |
| Bx Proven ABMR and Strong DSA s/p IVIG | 1.7 | 1.1 | — | — | DQ8 RIS 10 | DQ8 RIS 10 |

Briefly, 3 patients with primary GN and NS showed rapid and significant response to Obinutuzumab. One patient with recurrent SLE showed rapid resolution of symptoms and decline in anti-dsDNA antibodies (from 1:640 to 1:20) in 2 weeks. Patients with Rituximab-resistant MCD showed rapid improvements in proteinuria and resolution of NS in 2 cases. In 3 patients with recurrent GN, reduction in proteinuria and stabilization of SCr was seen. 2 out of 3 patients with Rituximab-resistant ABMR showed reductions in DSAs and had stable SCr.

These data with Obinutuzumab in renal transplant and GN patients suggests that Obinutuzumab appears safe and has efficacy beyond that seen with Rituximab. This is likely due to Obinutuzumab's novel mechanism of action (MOA) that results in superior B-cell depletion compared to Rituximab.

Example 3

Here we examine the safety and limited efficacy of Obinutuzumab in patients with severe nephrotic syndrome, autoimmune diseases and antibody mediated rejection (ABMR) who had failed multiple treatments including Rituximab. A total of 25 patients were treated with Obinutuzumab, 12 patients with steroid-resistant and Rituximab-resistant nephrotic syndrome, membranous SLE, membraneoproliferative GN (MPGN) and primary membranous glomerulonephritis and 13 post kidney transplant patients with biopsy proven ABMR with presence of donor specific antibody (DSA) who failed to respond to Rituximab. Patients with ABMR were treated with Obinutuzumab day 1 (100 mg), day 2 (900 mg). Patients with nephrotic syndrome were treated with Obinutuzumab day 1 (100 mg), day 2 (900 mg), and day 15 (1000 mg) as per CLL dosing guidelines. Premedication of acetaminophen 650 mg oral, diphenhydramine 25-50 mg oral, and solumedrol 40-80 mg intravenous was administered 30 minutes prior to each infusion. Patients were monitored for relevant clinical and laboratory parameters specific to their condition which included: DSAs (pre and 1M post-treatment), SCr, and degrees of proteinuria. Patients with ABMR had before and 1 month post treatment renal function and DSAs assessed. There were 4 of 13 patients who did not have post treatment DSAs drawn. All infusions were monitored for infusion-related AEs and long-term assessments of AEs/SAEs were also carried out.

TABLE 2

Demographic Table of Rituximab Resistant Nephrotic Syndrome Patients (N-12). Most Recent Serum Creatinine and DSA RIS were 1-2 M post Obinutuzumab (GAZYVA ®) treatment.

| | N = 12 | P |
|---|---|---|
| M/F | 5/7 | |
| Mean Age (y) | 49.8 ± 21.8 (19-83) | |
| Nephrotic Syndrome | | |
| FSGS | 4 | |
| MGN | 3 | |
| SLE | 1 | |
| MCD | 2 | |
| IgG-4 Related Disease | 1 | |
| MPGN type 1 | 1 | |
| Mean Serum Cr (mg/dl) | | |
| Pre GAZYVA ® | 1.8 ± 0.9 | |
| 1 M Post GAZYVA ® | 1.5 ± 0.9 | 0.015 |
| 3 M Post | 1.7 ± 1.1 | 0.164 |
| 6 M Post | 1.6 ± 1.4 | 0.961 |
| 12 M Post | 1.6 ± 1 | |
| Mean Urine Total Protein/Cr | | |
| Pre GAZYVA ® | 13.3 ± 11.2 | |
| 1 M Post GAZYVA ® | 5.1 ± 3.7 | 0.016 |
| 2 M Post | 3.7 ± 4 | 0.012 |
| 4 M Post | 1.7 ± 1.8 | 0.055 |
| 6 M Post | 0.4 ± 0.4 | 0.16 |
| 12 M Post | 0.7 | |

TABLE 3

Demographic Table of Post Kidney Transplant Patients with Rituximab Resistant ABMR.

| | N = 13 | P |
|---|---|---|
| M/F | 7/6 | |
| Mean Age (y) | 44.1 ± 15.1 (17-67) | |
| LD/DD | 5/8 | |
| Mean Serum Cr (mg/dl) | | 0.896 |
| Pre GAZYVA ® | 1.92 ± 0.67 | |
| Most Recent Post GAZYVA ® | 1.87 ± 0.93 | |
| Mean DSA RIS* | | 0.187 |
| Pre GAZYVA ® | 11.77 ± 11.65 | |
| Most Recent Post GAZYVA ® | 9.67 ± 8.93 | |
| Mean Time from Transplant to Treatment | 7.22 ± 5.44 | |

*Relative Intensity Scale (RIS) [0 points = No DSA; 2 points = <5000MFI {weak}; 5 points = 5000-10,000 MFI {moderate}; 10 points = >10,000MFI {strong}]. Most Recent Serum Creatinine and DSA RIS were 1-2 M post Obi treatment.

From this preliminary experience with Obinutuzumab for the treatment of Rituximab and steroid resistant nephrotic syndrome and GN (see Table 2), we saw significant benefits in reducing proteinuria up to one year post treatment as well as improvements in serum creatinine (mg/dl). No major AE/SAEs including infusion related side effects were seen in this patient population. For post-kidney transplant patients with Rituximab resistant ABMR (see Table 3), no significant differences for DSAs in aggregate were seen however specific patients showed reductions within one to three months post treatment, with improvement in serum creatinine. One post-transplant Obinutuzumab treated patient developed CMV viremia and another developed both *C. diff* colitis and urinary tract infection (UTI) which resolved with treatment.

Figure 5:
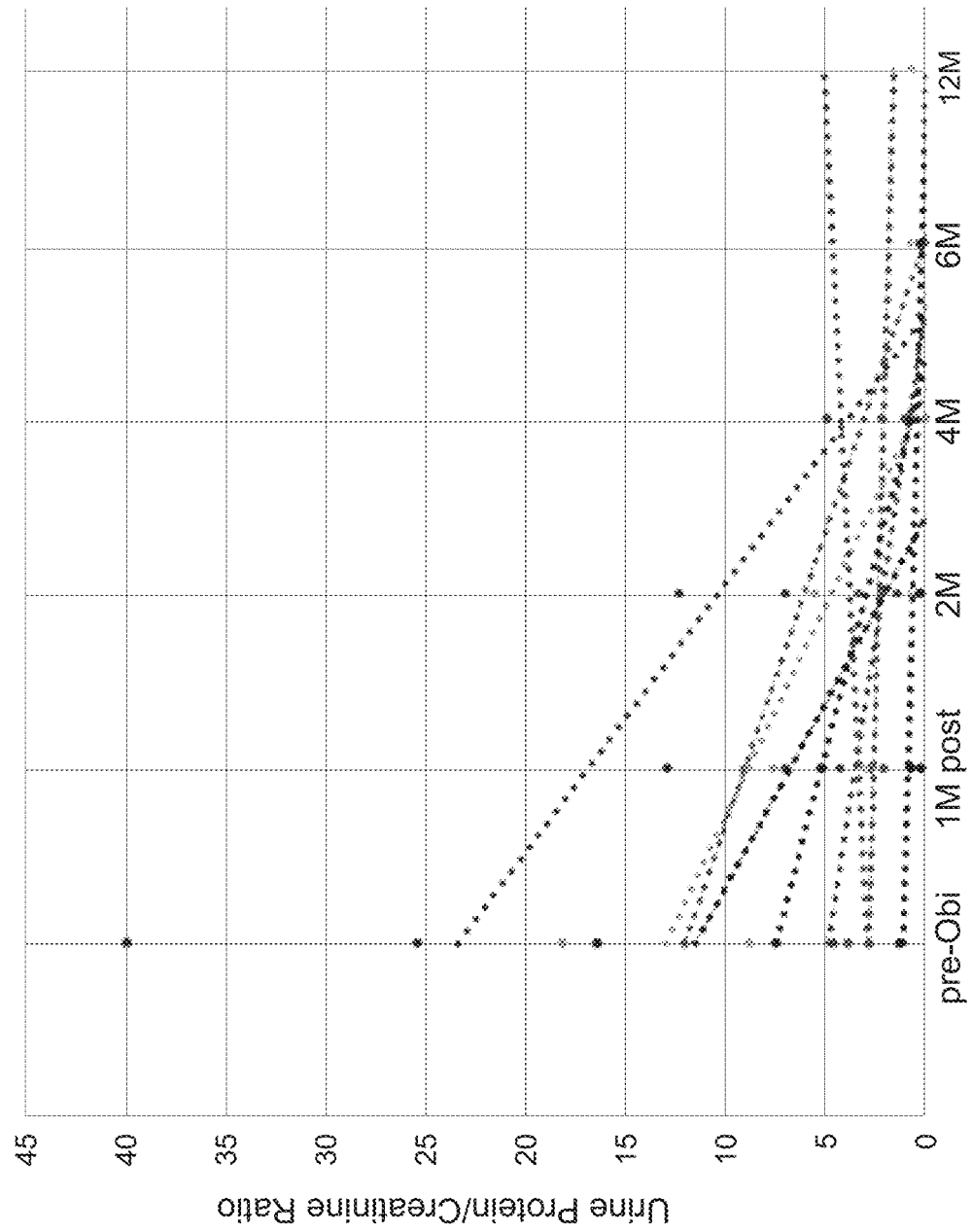
FIG. 5 depicts in accordance with various embodiments of the invention, pre- and post-Obi urine total protein/creatinine ratios (UTP/Cr) through 12M with linear trends of the 12 nephrotic syndrome patients.

FIG. 5 shows pre-Obinutuzumab urine total protein/creatinine ratios (UTP/Cr) through 12M post-Obi treatment with linear trends of the 12 nephrotic syndrome patients. Significant improvements of UTP/Cr were seen over the 12 month period post treatment.

Figure 6:
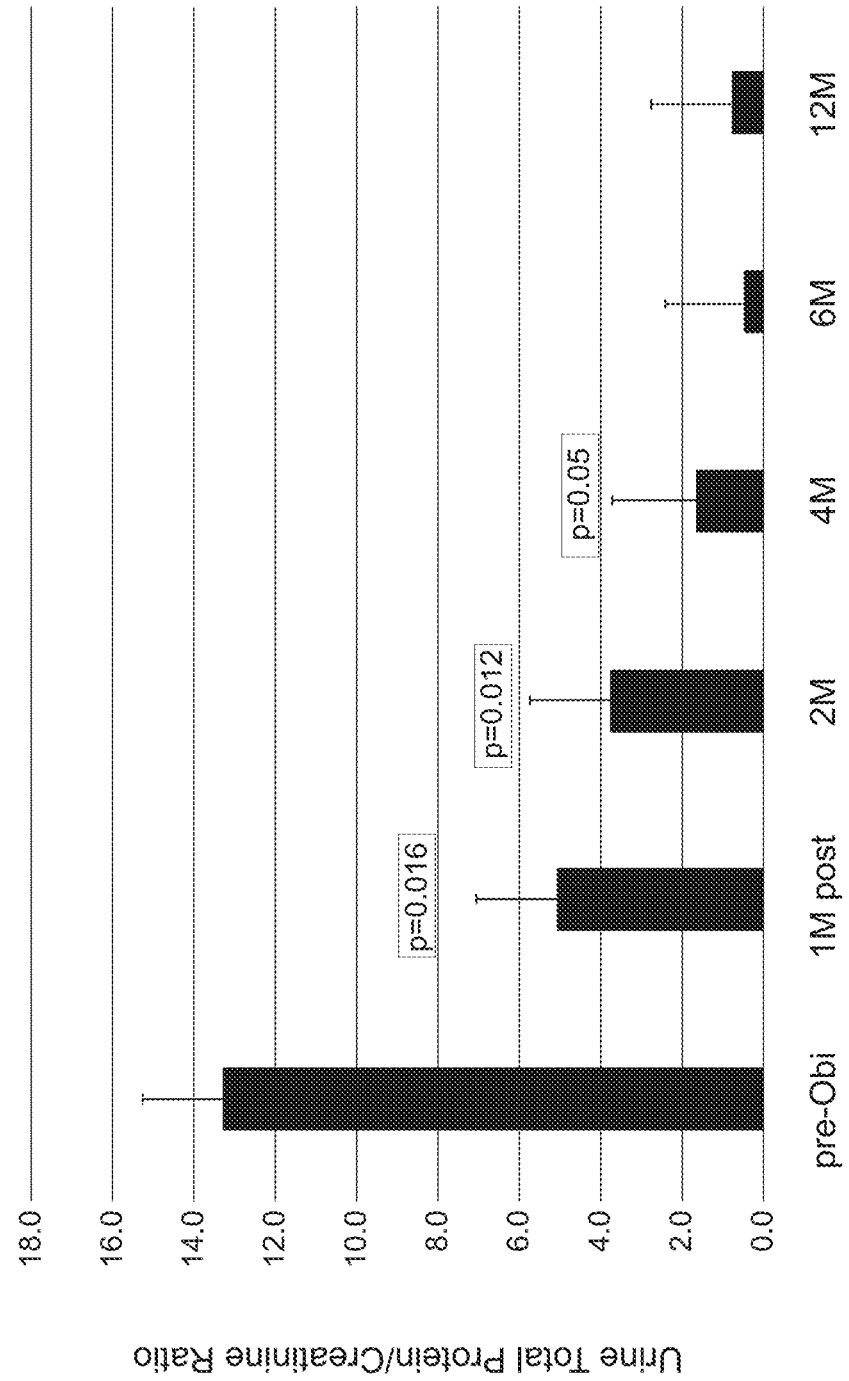
FIG. 6 depicts in accordance with various embodiments of the invention, UTP/Cr values over time. Significant reductions were seen in these values after Obi therapy in the nephrotic syndrome patients.

FIG. 6 shows pre-Obinutuzumab UTP/Cr through 12M post-Obinutuzumab treatment. Significant reductions were seen at 1 month post treatment (p=0.016), 2 month post treatment (p=0.0012) and 4 month post treatment (p=0.05) compared to baseline.

Figure 7:
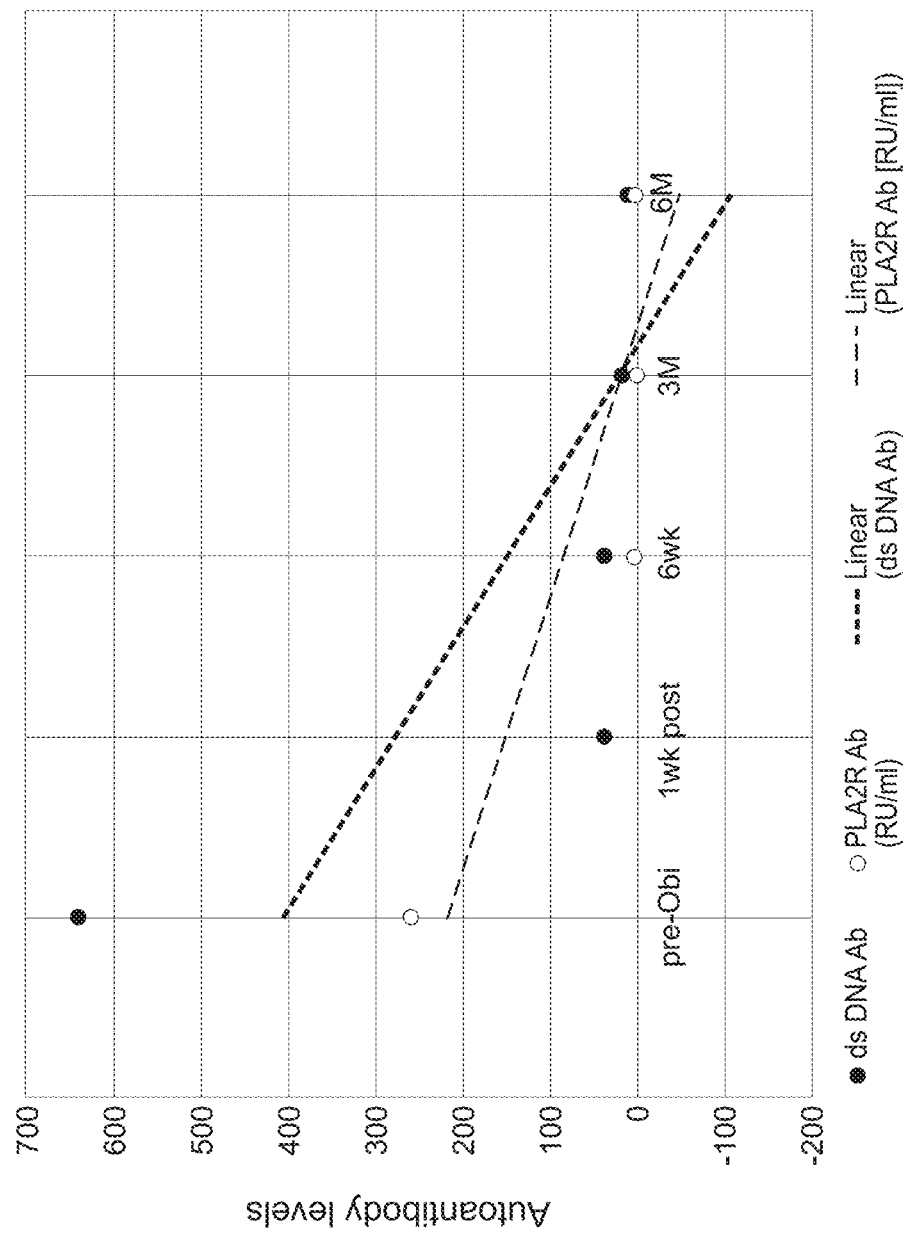
FIG. 7. depicts in accordance with various embodiments of the invention, the effects of Obi on anti-PLA2R in a patient with primary MGN and anti-dsDNA antibodies in a patient with membranous SLE.

FIG. 7 shows linear trends of autoantibody levels at pre-Obinutuzumab up to 6M post Obinutuzumab. Trends show non-significant decrease of autoantibody levels from baseline.

Figure 8:
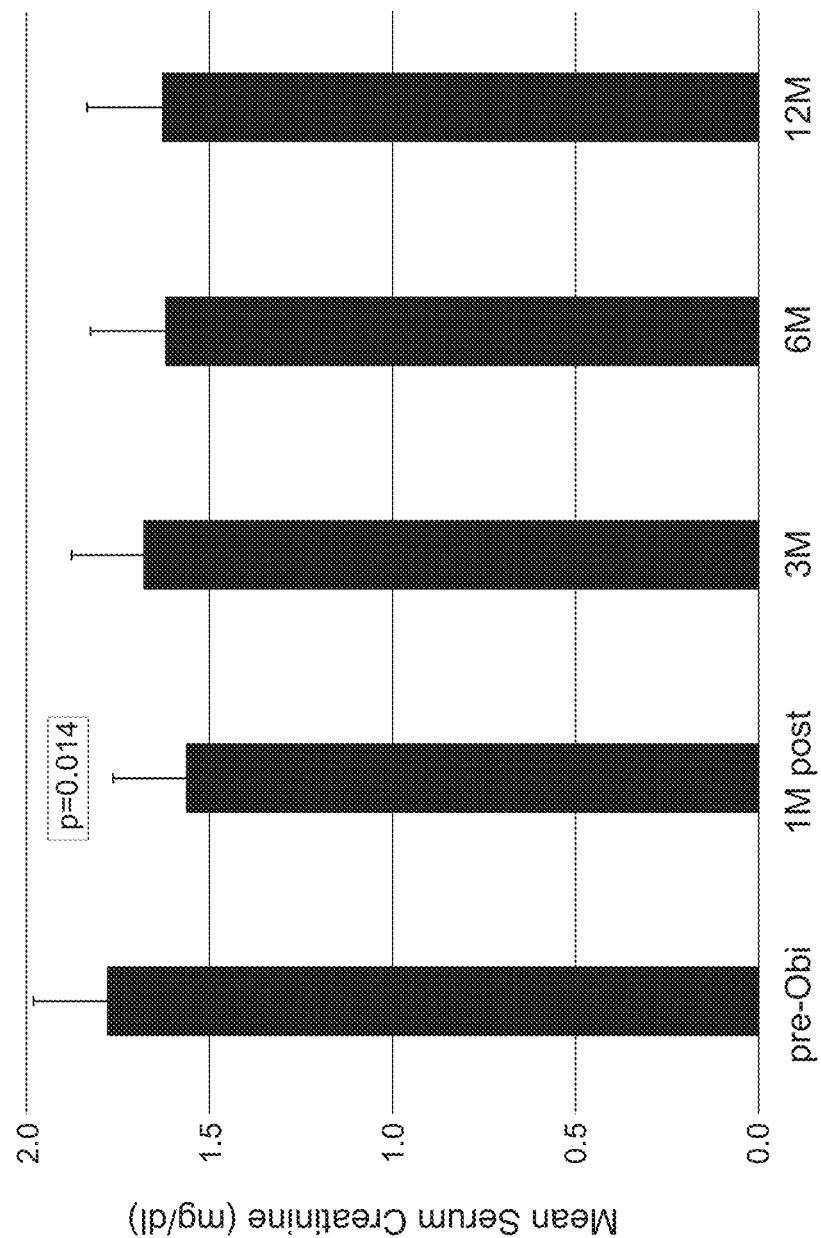
FIG. 8 depicts in accordance with various embodiments of the invention, mean serum creatinine (mg/dl) values post treatment in the nephrotic syndrome patients. Significance was seen at 1M post treatment but overall creatinine remained stable in this patient population.

FIG. 8 shows mean serum creatinine (Cr, mg/dl) from pre-Obinutuzumab up to 12 months post Obinutuzumab. Significant decrease was seen at one month post Obinutuzumab, p=0.014, and overall Cr remained stable from baseline up to 12 month post treatment.

Based on the effects of Obinutuzumab treatment of patients with glomerular diseases and ABMR, we can conclude that the drug appears safe when administered to patients with these difficult conditions who have failed multiple other therapies. The most impressive findings were the reversal of NS and elimination of pathogenic autoantibodies. Obinutuzumab stabilized renal function but did not significantly decrease DSAs over this short observation period in patients with ABMR.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings.

The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The invention claimed is:

1. A method of treating, inhibiting or reducing severity of nephrotic syndrome or glomerulonephritis in a subject in need thereof, wherein the subject is a transplant recipient, the method consisting of:
    administering an effective amount of an anti-CD20 antibody, or a pharmaceutical composition consisting of the anti-CD20 antibody and a pharmaceutically acceptable excipient, in two or more doses over a period of no more than 21 days to the subject after transplantation, or
    administering an effective amount of the anti-CD20 antibody or the pharmaceutical composition in the two or more doses over a period of no more than 21 days and a standard-of-care treatment to the subject,
    wherein the anti-CD20 antibody comprises Obinutuzumab, so as to treat, inhibit or reduce the severity of nephrotic syndrome or glomerulonephritis in the subject.

2. The method of claim 1, for treating, inhibiting or reducing the severity of glomerulonephritis in the subject in need thereof, and the glomerulonephritis is membranous glomerulonephritis.

3. The method of claim 1, wherein the glomerulonephritis is membranous glomerulonephritis, focal segmental glomerulosclerosis (FSGS), minimal change nephrotic syndrome, cryoglobulinemic glomerulonephritis, or IgA nephropathy.

4. The method of claim 1, wherein the anti-CD20 antibody comprises Obinutuzumab and Rituximab.

5. The method of claim 1, wherein the subject has Rituximab-resistant nephrotic syndrome or the subject has relapsed from a previous rituximab treatment.

6. The method of claim 1, wherein the nephrotic syndrome in the subject is caused by any one or more of minimal change disease, focal segmental glomerulosclerosis, membranous glomerulonephritis, IgA nephropathy and cryoglobulinemic glomerulonephritis.

7. The method of claim 1, wherein the subject has been administered a standard-of-care treatment prior to the administration of the anti-CD20 antibody.

8. The method of claim 7, wherein the subject does not respond to the standard-of-care treatment prior to the administration of the anti-CD20 antibody.

9. The method of claim 1, consisting of the administration of the anti-CD20 antibody or the pharmaceutical composition and the standard-of-care treatment, wherein the anti-CD20 antibody is administered simultaneously or sequentially with the standard-of-care treatment.

10. The method of claim 7, wherein the standard-of-care treatment is any one or more of a steroid, mycophenolic acid, mycophenolate mofetil, and a calcineurin inhibitor, wherein the calcineurin inhibitor comprises cyclosporine, tacrolimus, or a combination thereof.

11. The method of claim 1, wherein the effective amount of the anti-CD20 antibody is about 0.1 to 1000 mg of the anti-CD20 antibody/kg of the subject/day.

12. The method of claim 1, wherein the anti-CD20 antibody is administered to the subject 1-3 times per day or 1-7 times per week.

13. The method of claim 1, wherein the anti-CD20 antibody is Obinutuzumab, which is administered to the subject for 1-5 days.

14. The method of claim 1, wherein the effective amount is two doses of 1 g Obinutuzumab per dose, wherein a first dose is administered on the same day or over two days.

15. The method of claim 14, wherein the Obinutuzumab is administered intravenously.

16. The method of claim 14, wherein the two doses are administered 15 days apart.

17. The method of claim 14, wherein the first dose is administered in an amount of 100 mg on day 1 and 900 mg on day 2.

18. The method of claim 1, wherein the subject is human.

19. A method of treating, inhibiting or reducing severity of lupus nephritis in a subject in need thereof, wherein the subject is a transplant recipient, the method consisting of: administering an effective amount of an anti-CD20 antibody, or a pharmaceutical composition consisting of the anti-CD20 antibody and a pharmaceutically acceptable excipient, in two or more doses over a period of no more than 21 days to the subject during or after the subject receives a kidney transplant, or administering an effective amount of the anti-CD20 antibody or the pharmaceutical composition in the two or more doses over a period of no more than 21 days and a standard-of-care treatment to the subject during or after the subject receives a kidney transplant, wherein the anti-CD20 antibody comprises Obinutuzumab, so as to treat, inhibit or reduce the severity of lupus nephritis in the subject.

20. The method of claim 1, wherein the subject is a kidney transplant recipient.

* * * * *